(12) United States Patent
Chowdhury et al.

(10) Patent No.: US 11,638,527 B2
(45) Date of Patent: May 2, 2023

(54) DETERMINATION OF CARDIOPULMONARY SIGNALS FOR MULTI-PERSONS USING IN-BODY SIGNALS OBTAINED BY UWB RADAR

(71) Applicant: Tata Consultancy Services Limited, Mumbai (IN)

(72) Inventors: Arijit Chowdhury, Kolkata (IN); Smriti Rani, Kolkata (IN); Anwesha Khasnobish, Kolkata (IN); Taniya Das, Kolkata (IN); Tapas Chakravarty, Kolkata (IN); Arpan Pal, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 245 days.

(21) Appl. No.: 17/156,395

(22) Filed: Jan. 22, 2021

(65) Prior Publication Data

US 2021/0401296 A1   Dec. 30, 2021

(30) Foreign Application Priority Data

Jun. 29, 2020  (IN) .............................. 202021027589

(51) Int. Cl.
*A61B 5/0205*   (2006.01)
*A61B 5/05*   (2021.01)
(Continued)

(52) U.S. Cl.
CPC .............. *A61B 5/0205* (2013.01); *A61B 5/05* (2013.01); *A61B 5/1072* (2013.01); *A61B 5/721* (2013.01);
(Continued)

(58) Field of Classification Search
None
See application file for complete search history.

(56) References Cited

U.S. PATENT DOCUMENTS

| 7,567,200 B1 * | 7/2009 | Osterweil | ............... G01S 13/56 342/28 |
| 2005/0096523 A1 * | 5/2005 | Vass | ...................... A61B 6/032 600/407 |

(Continued)

FOREIGN PATENT DOCUMENTS

| CA | 3064083 A1 | 11/2018 | |
| JP | 2007202297 A * | 8/2007 | ............. A61B 5/107 |

OTHER PUBLICATIONS

Rahko, "Evaluation of the Skin-To-Heart Distance in the Standing Adult by Two-Dimensional Echocardiography," Journal of the American Society of Echocardiography, vol. 21, Issue 6, Jun. 2008, pp. 761-764. (Year: 2008).*

(Continued)

*Primary Examiner* — Joel Lamprecht
*Assistant Examiner* — Ashish S Jasani
(74) *Attorney, Agent, or Firm* — Finnegan, Henderson, Farabow, Garrett & Dunner LLP

(57) ABSTRACT

The disclosure herein generally relates to the field of determination of cardiopulmonary signals for multi-persons, and, more particularly, to determination of cardiopulmonary signals for multi-persons using in-body signals obtained by ultra-wide band (UWB) radar. The disclosed method determines of cardiopulmonary signals for multi-persons using in-body signals, wherein a UWB radar signals/waves reflected from inside a human body is utilized for efficient determination of cardiopulmonary signals. The disclosed method and system utilize the UWB radar signals to identify a number of persons along with several details about the persons that include a girth of the each identified person and the orientation of the identified person towards the one or more UWB radar. Further a chest wall distance, a breathing rate, a heart wall distance and a heart rate are determined for (Continued)

all the identified persons based on the identified girth and the identified orientation along with the UWB radar signals.

15 Claims, 20 Drawing Sheets

(51) Int. Cl.
    *A61B 5/00*     (2006.01)
    *A61B 5/107*     (2006.01)
    *A61B 5/0245*     (2006.01)
    *A61B 5/08*     (2006.01)

(52) U.S. Cl.
    CPC ............ *A61B 5/725* (2013.01); *A61B 5/7246* (2013.01); *A61B 5/742* (2013.01); *A61B 5/0245* (2013.01); *A61B 5/0816* (2013.01)

(56) References Cited

U.S. PATENT DOCUMENTS

| | | | | |
|---|---|---|---|---|
| 2015/0223733 | A1* | 8/2015 | Al-Alusi | G01S 7/415 |
| | | | | 600/407 |
| 2018/0279884 | A1* | 10/2018 | Ahmad | A61B 5/725 |

OTHER PUBLICATIONS

Khan, Faheem et al., "A Detailed Algorithm for Vital Sign Monitoring of a Stationary/Non-Stationary Human through IR-UWB Radar", Sensors for Globalized Healthy Living and Wellbeing, 2017 vol. 17(2), MDPI, https://www.mdpi.com/1424-8220/17/2/290/pdf.
Hashemi, Amjad et al., "An Efficient Algorithm for Remote Detection of Simulated Heart Rate Using Ultra-Wide Band Signals", American Journal of Biomedical Engineering, 2013, vol. 3(6), pp. 199-207, Research Gate, http://www.sapub.org/global/showpaperpdf.aspx?doi=10.5923/j.ajbe.20130306.09.
Woo, Jeong et al., Multi-Human Detection Algorithm Based on an Impulse Radio Ultra Wideband Radar System, Access, 2016, vol. 4, IEEE, https://ieeexplore.ieee.org/stamp/stamp.jsp?tp=&arnumber=7803603.
Le, Minhbuy et al., "Multivariate Correlation of Higher Harmonics for Heart Rate Remote Measurement using UWB Impulse Radar", Title of the item: Sensors Journal, 2019, vol. 20 (4), pp. 1859-1866, IEEE, https://www.researchgate.net/publication/336949794_Multivariate_Correlation_of_Higher_Harmonics_for_Heart_Rate_Remote_Measurement_Using_UWB_Impulse_Radar/link/5dc02e77299bf1a47b11ff93/download.
Communication about intention to grant a European Patent received from the European Patent Office in EP Application No. 21 152 743.7, 8 pages, dated Apr. 4, 2022.
Extended European Search Report issued by the European Patent Office in counterpart European Patent Application No. 21 152 743.7, 3 pages, dated Jul. 15, 2021.
Dusan Kocur et al., "Estimation of Breathing Frequency and Heart Rate by Biometric UWB Radar", 2018 IEEE International Conference on Systems, Man, and Cybernetics, pp. 2570-2576, (2018).
Wang Pengfei et al: "Noncontact Heart Rate Measurement Based on an Improved Convolutional Sparse Coding Method Using I R-UWB Radar", IEEE Access, vol. 7, pp. 158492-158502, (2019).
Baird Zachary et al: "Classification of Human Posture from Radar Returns Using Ultra-Wideband Radar", 2018 40th Annual International Conference of the IEEE Engineering in Medicine and Biology Society (EMBC), IEEE, pp. 3268-3271, (2018).
Kocur Dusan et al: "Multiple Person Localization Based on their Vital Sign Detection Using UWB Sensor", Microwave Systems and Applications, Chapter 17, pp. 399-422 , (2017).

\* cited by examiner

DETERMINATION OF CARDIOPULMONARY SIGNALS FOR MULTI-PERSONS USING IN-BODY SIGNALS OBTAINED BY UWB RADAR

CROSS-REFERENCE TO RELATED APPLICATIONS AND PRIORITY

The present application claims priority from Indian provisional application no. 202021027589, filed on Jun. 29, 2020.

TECHNICAL FIELD

The disclosure herein generally relates to the field of determination of cardiopulmonary signals for multiple-persons using UWB radar, and, more particularly, to determination of cardiopulmonary signals for multi-persons using in-body signals obtained by Ultra-wide band (UWB) radar.

BACKGROUND

Signals emanating from the heart and lungs contain valuable information about the cardiopulmonary system. Unobtrusive monitoring these cardiopulmonary signals longitudinally can detect early pathological symptoms as the cardiopulmonary signals convey physiological parameters that are essential for a comprehensive evaluation of the health status of individuals and hence ensure care accordingly.

There are several well-known techniques for determination of cardiopulmonary signals, of which determination of cardiopulmonary signals using UWB radar is popular due to several advantages UWB radar offers such as unobstructed sensing, efficient detection of cardiopulmonary signals. However, existing techniques for determination of cardiopulmonary signals measure the vibrations of chest wall, wherein vibration from both heart and breathing is considered and compared. The determination of cardiopulmonary signals based vibrations of chest may not be very efficient as the breathing vibration is more dominant compared to heart vibration, hence difficult to obtain heart vibration signal. Further the vibrations can also be highly attenuated, and this leads to much more error prone determination of cardiopulmonary signals. Further there are efficient techniques available for detection of cardiopulmonary signals from single person, however efficient determination of cardiopulmonary signals for multiple persons is still a research subject matter.

SUMMARY

Embodiments of the present disclosure present technological improvements as solutions to one or more of the above-mentioned technical problems recognized by the inventors in conventional systems. For example, in one embodiment, determination of cardiopulmonary signals for multi-persons using in-body signals obtained by Ultra-wide band (UWB) radar is provided.

In an aspect a method for determination of cardiopulmonary signals for multi-persons using in-body signals obtained by Ultra-wide band (UWB) radar. The method further includes receiving, by the one or more hardware processors, an input data set from the one or more UWB radars, wherein the input data is a UWB radar signal comprising 2-dimensional matrix indicative of a reflectance intensity at a range of the one or more UWB radar for a plurality of time instances. The method further includes preprocessing, by the one or more hardware processors, the input data set based on a filtering technique, a motion detection technique, and an envelope detection technique to obtain a pre-processed matrix, wherein the pre-processed matrix comprises of a plurality of range bins for a plurality of instances of range bin time. The method further includes identifying, by the one or more hardware processors, a plurality of persons in the vicinity of the one or more UWB radar and a girth for each of the person of the plurality of persons using the pre-processed matrix based on a peak identification technique, wherein the girth of the each person comprises of an entry point and an exit point, where the entry point and the exit point are indicative of a category of the person's body type. The method further includes identifying, by the one or more hardware processors, an orientation for each of the identified person of the plurality of persons using the pre-processed matrix based on a plurality of comparison techniques, wherein the orientation is indicative of the orientation of the identified person with respect to the one or more UWB radar, wherein the plurality of comparison techniques comprises an intensity comparison technique and a spectral flatness comparison technique. The method further includes determining, by the one or more hardware processors, a chest wall distance for each of the identified person of the plurality of persons using the pre-processed matrix based on the peak identification technique, wherein the chest wall distance is indicative of distance between the one or more UWB radar and each the identified person's chest wall. The method further includes determining, by the one or more hardware processors, a breathing rate for each of the identified person of the plurality of persons using the pre-processed matrix and the chest wall distance based on a plurality of auto-correlation technique, wherein the plurality of auto-correlation techniques are implemented on a set of time series of the range bins extracted from the pre-processed matrix using the chest wall distance. The method further includes determining, by the one or more hardware processors, a heart wall distance for each of the identified person of the plurality of persons and a heart wall range bin for each of the identified person of the plurality of persons based on a heart wall distance determination technique wherein: the heart wall distance is indicative of distance between each of the identified person's chest wall and each of the identified person's heart wall and the heart wall distance is determined using a set of pre-defined dielectric constant of a plurality of biological tissues, a set of pre-defined wall values of the plurality of biological tissues, a pre-defined scaling factor for each of the biological tissue and the heart wall range bin is indicative of a number of the range bin between each of the identified person's heart wall and the one or more UWB radar and the heart wall range bin is determined using the heart wall distance, the chest wall distance and a pre-determined range resolution of the one or more UWB radar. The method further includes determining, by the one or more hardware processors, a heart rate for each of the identified person of the plurality of persons using the pre-processed matrix, the heart wall distance and a pre-determined time resolution of the one or more UWB radar based on a heart rate determination technique, heart rate determination technique comprises of a frequency domain technique and a harmonic removal technique. The method further includes displaying, by the one or more hardware processors, the determined heart rate and the determined breathing rate, wherein the determined heart rate and the determined breathing rate is indicative of the cardiopulmonary signals.

In another aspect, a system for determination of cardiopulmonary signals for multi-persons using in-body signals obtained by an Ultra-wide band (UWB) radar is provided. The system is configured for receiving an input data set from one or more one or more UWB radars, wherein the input data is a UWB radar signal comprising 2-dimensional matrix indicative of a reflectance intensity at a range of the one or more UWB radar for a plurality of time instances. The system is further configured for preprocessing, by the one or more hardware processors, the input data set based on a filtering technique, a motion detection technique, and an envelope detection technique to obtain a pre-processed matrix, wherein the pre-processed matrix comprises of a plurality of range bins for a plurality of instances of range bin time. The system is further configured for identifying, by the one or more hardware processors, a plurality of persons in the vicinity of the one or more UWB radar and a girth for each of the person of the plurality of persons using the pre-processed matrix based on a peak identification technique, wherein the girth of the each person comprises of an entry point and an exit point, where the entry point and the exit point are indicative of a category of the person's body type. The system is further configured for identifying, by the one or more hardware processors, an orientation for each of the identified person of the plurality of persons using the pre-processed matrix based on a plurality of comparison techniques, wherein the orientation is indicative of the orientation of the identified person with respect to the one or more UWB radar, wherein the plurality of comparison techniques comprises an intensity comparison technique and a spectral flatness comparison technique. The system is further configured for includes determining, by the one or more hardware processors, a chest wall distance for each of the identified person of the plurality of persons using the pre-processed matrix based on the peak identification technique, wherein the chest wall distance is indicative of distance between the one or more UWB radar and each the identified person's chest wall. The system is further configured for determining, by the one or more hardware processors, a breathing rate for each of the identified person of the plurality of persons using the pre-processed matrix and the chest wall distance based on a plurality of auto-correlation technique, wherein the plurality of auto-correlation techniques are implemented on a set of time series of the range bins extracted from the pre-processed matrix using the chest wall distance. The system is further configured for determining, by the one or more hardware processors, a heart wall distance for each of the identified person of the plurality of persons and a heart wall range bin for each of the identified person of the plurality of persons based on a heart wall distance determination technique wherein: the heart wall distance is indicative of distance between each of the identified person's chest wall and each of the identified person's heart wall and the heart wall distance is determined using a set of pre-defined dielectric constant of a plurality of biological tissues, a set of pre-defined wall values of the plurality of biological tissues, a pre-defined scaling factor for each of the biological tissue and the heart wall range bin is indicative of a number of the range bin between each of the identified person's heart wall and the one or more UWB radar and the heart wall range bin is determined using the heart wall distance, the chest wall distance and a pre-determined range resolution of the one or more UWB radar. The system is further configured for determining, by the one or more hardware processors, a heart rate for each of the identified person of the plurality of persons using the pre-processed matrix, the heart wall distance and a pre-determined time resolution of the one or more UWB radar based on a heart rate determination technique, heart rate determination technique comprises of a frequency domain technique and a harmonic removal technique. The system is further configured for displaying, by the one or more hardware processors, the determined heart rate and the determined breathing rate, wherein the determined heart rate and the determined breathing rate is indicative of the cardiopulmonary signals.

In yet another aspect, a non-transitory computer readable medium for a determination of cardiopulmonary signals for multi-persons using in-body signals obtained by an Ultra-wide band (UWB) radar is provided. The program includes receiving an input data set from one or more ultra-wideband (UWB) radars, wherein the input data is a UWB radar signal comprising 2-dimensional matrix indicative of a reflectance intensity at a range of the one or more UWB radar for a plurality of time instances. The program further includes preprocessing, by the one or more hardware processors, the input data set based on a filtering technique, a motion detection technique, and an envelope detection technique to obtain a pre-processed matrix, wherein the pre-processed matrix comprises of a plurality of range bins for a plurality of instances of range bin time. The program further includes identifying, by the one or more hardware processors, a plurality of persons in the vicinity of the one or more UWB radar and a girth for each of the person of the plurality of persons using the pre-processed matrix based on a peak identification technique, wherein the girth of the each person comprises of an entry point and an exit point, where the entry point and the exit point are indicative of a category of the person's body type. The program further includes identifying, by the one or more hardware processors, an orientation for each of the identified person of the plurality of persons using the pre-processed matrix based on a plurality of comparison techniques, wherein the orientation is indicative of the orientation of the identified person with respect to the one or more UWB radar, wherein the plurality of comparison techniques comprises an intensity comparison technique and a spectral flatness comparison technique. The program further includes determining, by the one or more hardware processors, a chest wall distance for each of the identified person of the plurality of persons using the pre-processed matrix based on the peak identification technique, wherein the chest wall distance is indicative of distance between the one or more UWB radar and each the identified person's chest wall. The program further includes determining, by the one or more hardware processors, a breathing rate for each of the identified person of the plurality of persons using the pre-processed matrix and the chest wall distance based on a plurality of auto-correlation technique, wherein the plurality of auto-correlation techniques are implemented on a set of time series of the range bins extracted from the pre-processed matrix using the chest wall distance. The program further includes determining, by the one or more hardware processors, a heart wall distance for each of the identified person of the plurality of persons and a heart wall range bin for each of the identified person of the plurality of persons based on a heart wall distance determination technique wherein: the heart wall distance is indicative of distance between each of the identified person's chest wall and each of the identified person's heart wall and the heart wall distance is determined using a set of pre-defined dielectric constant of a plurality of biological tissues, a set of pre-defined wall values of the plurality of biological tissues, a pre-defined scaling factor for each of the biological tissue and the heart wall range bin is indicative of a number of the range bin between each of the identified person's heart wall and the one or more UWB radar and the heart wall range bin is determined using the heart wall distance, the chest wall distance and a pre-determined range resolution of the one or more UWB radar. The program further includes determining, by the one or more hardware processors, a heart rate for each of the identified person of the plurality of persons using the pre-processed matrix, the heart wall distance and a pre-determined time resolution of the one or more UWB radar based on a heart rate determination technique, heart rate determination technique comprises of a frequency domain technique and a harmonic removal technique. The program further includes displaying, by the one or more hardware processors, the determined heart rate and the determined breathing rate, wherein the determined heart rate and the determined breathing rate is indicative of the cardiopulmonary signals.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
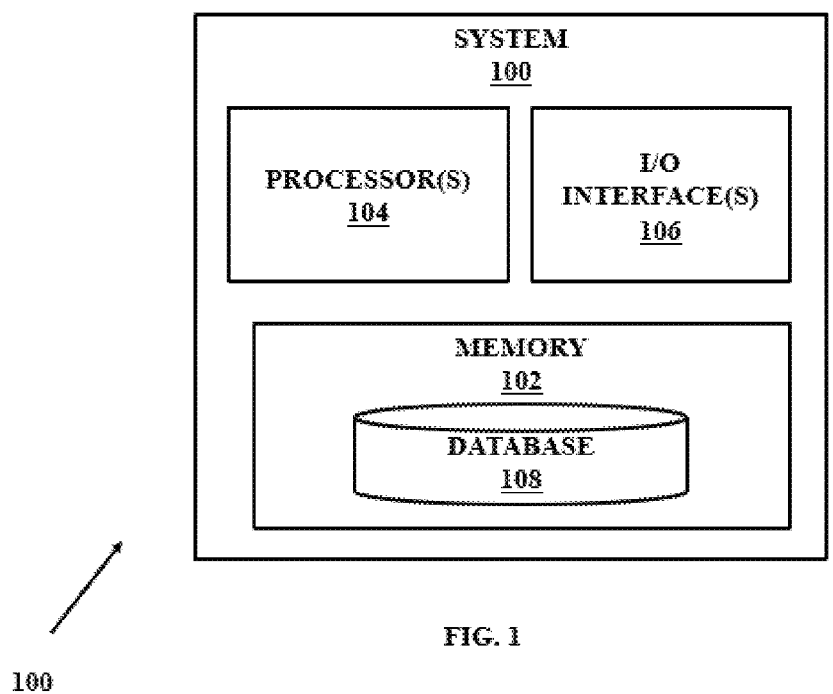
FIG. 1 illustrates a functional block diagram of an exemplary system for determination of cardiopulmonary signals for multi-persons using in-body signals obtained by Ultra-wide band (UWB) radar according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

The embodiments disclose a method and system for determination of cardiopulmonary signals for multi-persons using in-body signals obtained by an Ultra-wide band (UWB) radar. The disclosed method determines of cardiopulmonary signals for multi-persons using in-body signals, wherein a UWB radar signals/waves reflected from inside a human body is utilized for efficient determination of cardiopulmonary signals. The disclosed method and system utilize the UWB radar signals to identify a number of persons along with several details about the persons that include a girth of the each identified person and the orientation of the identified person towards the UWB radar. Further a chest wall distance, a breathing rate, a heart wall distance and a heart rate are determined for all the identified persons based on the identified girth and the identified orientation along with the UWB radar signals.

Referring now to the drawings, and more particularly to FIG. 1 through FIG. 18 where similar reference characters denote corresponding features consistently throughout the figures, there are shown preferred embodiments and these embodiments are described in the context of the following exemplary system and/or method.

FIG. 1 is a functional block diagram of a system 100 for determination of cardiopulmonary signals for multi-persons using in-body signals obtained by an Ultra-wide band (UWB) radar, in accordance with some embodiments of the present disclosure.

In an embodiment, the system 100 includes a processor(s) 104, communication interface device(s), alternatively referred as input/output (I/O) interface(s) 106, and one or more data storage devices or a memory 102 operatively coupled to the processor(s) 104. The system 100 with one or more hardware processors is configured to execute functions of one or more functional blocks of the system 100.

Referring to the components of system 100, in an embodiment, the processor(s) 104, can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 is configured to fetch and execute computer-readable instructions stored in the memory 102. In an embodiment, the system 100 can be implemented in a variety of computing systems including laptop computers, notebooks, hand-held devices such as mobile phones, workstations, mainframe computers, servers, a network cloud and the like.

The I/O interface(s) 106 can include a variety of software and hardware interfaces, for example, a web interface, a graphical user interface, a touch user interface (TUI) and the like and can facilitate multiple communications within a wide variety of networks N/W and protocol types, including wired networks, for example, LAN, cable, etc., and wireless networks, such as WLAN, cellular, or satellite. In an embodiment, the I/O interface (s) 106 can include one or more ports for connecting a number of devices (nodes) of the system 100 to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

Further, the memory 102 may include a database 108, which may store the dictionary, the vocabulary embedding matrix, the frequency vectors, the frequency matrix and the like. Thus, the memory 102 may comprise information pertaining to input(s)/output(s) of each step performed by the processor(s) 104 of the system 100 and methods of the present disclosure. In an embodiment, the database 108 may be external (not shown) to the system 100 and coupled to the system via the I/O interface 106. Functions of the components of system 100 are explained in conjunction with functional overview of the system 100 in FIG. 2 and flow diagram of FIGS. 3A and 3×6 for document embedding to obtain average embeddings for documents.

The system 100 supports various connectivity options such as BLUETOOTH®, USB, ZigBee and other cellular services. The network environment enables connection of various components of the system 100 using any communication link including Internet, WAN, MAN, and so on. In an exemplary embodiment, the system 100 is implemented to operate as a stand-alone device. In another embodiment, the system 100 may be implemented to work as a loosely coupled device to a smart computing environment. The components and functionalities of the system 100 are described further in detail.

Figure 2:
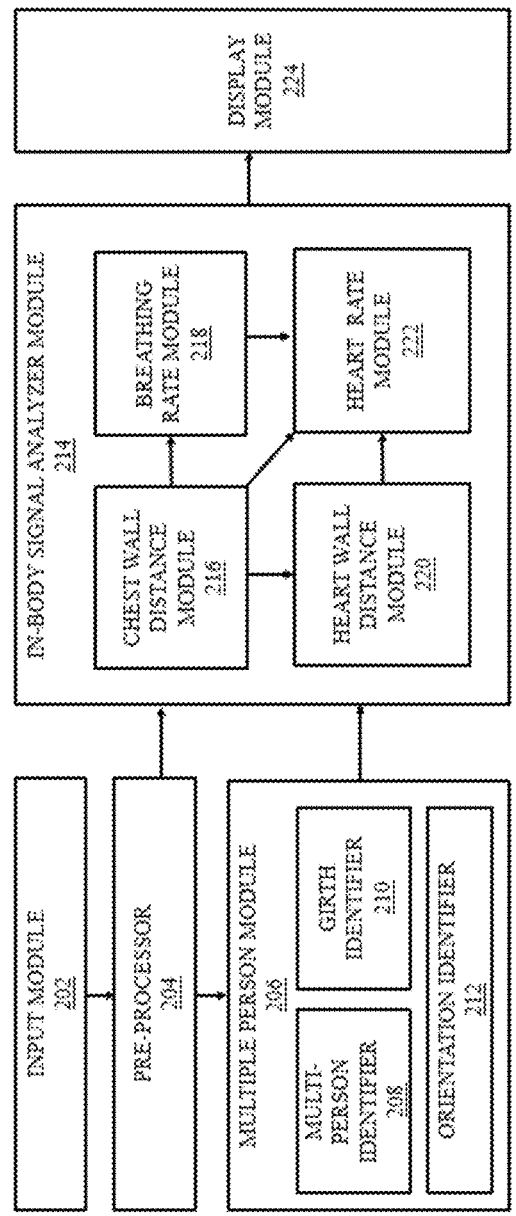
FIG. 2 is a functional block diagram for the system of FIG. 1 according to some embodiments of the present disclosure.

FIG. 2 is a functional block diagram of the system 100 of FIG. 1, in accordance with some embodiments of the present disclosure. As depicted in the architecture, the FIG. 2 illustrates the functions of the components of the system (100) for determination of cardiopulmonary signals for multi-persons using in-body signals obtained by Ultra-wide band (UWB) radar.

The system (100) comprises an input module 202 configured for receiving, by the one or more hardware processors, an input data set from one or more ultra-wideband (UWB) radars, wherein the input data is a UWB radar signal comprising 2-dimensional matrix indicative of a reflectance intensity at a range of the One or more UWB radar for a plurality of time instances.

In an embodiment, a Humatics™ P440 Ultra-Wide band (UWB) radar module is utilized. The input data obtained from the One or more UWB radar is a 2-dimensional matrix is indicative of a reflectance intensity at a range of the one or more UWB radar for a plurality of time instances, wherein x-axis of the 2-dimensional matrix is indicative of a range and y-axis of the 2-dimensional matrix is indicative of a time, hence a reflectance intensity is received for each range at an instant of time. The range refers to distance between an object (that reflects signal) and the one or more UWB radar, wherein the object can be living or non-living entity. Considering an example for one or more UWB radar configurations, a range is fixed and a time that can be dynamically updated based on a user requirement, wherein a range resolution of 0.0091 m for a time resolution of 139 ms is configured. For instance, for a 400×400 matrix of range time data, the radar data captured in the range from 0 to (400×0.0091)=3.64 m and the time for which data was collected is 0 to (400×139 ms)=55.6 seconds.

Figure 4:
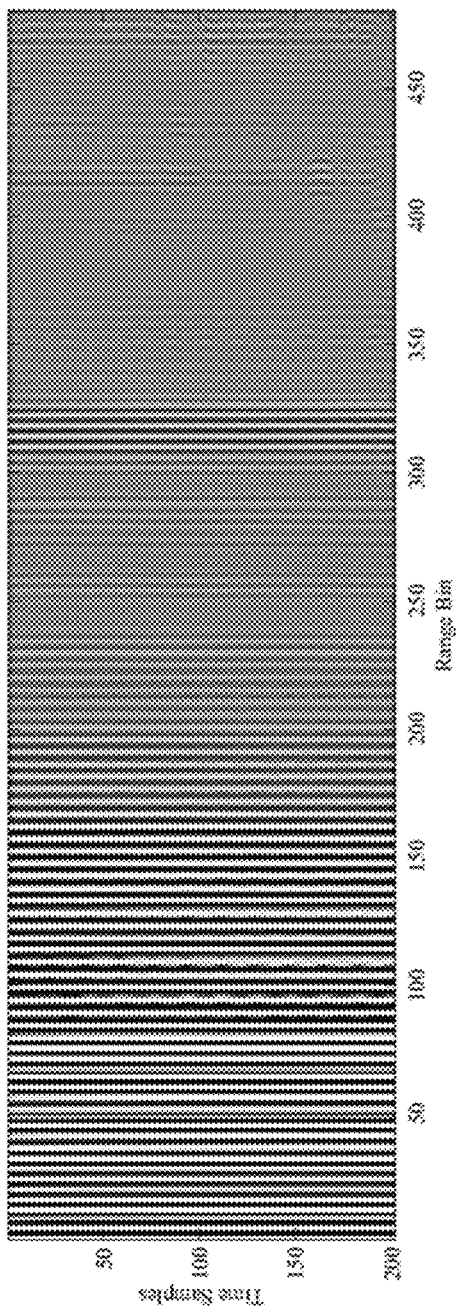
FIG. 4 illustrates a graph of the input data set received from a one or more UWB radar, in accordance with some embodiments of the present disclosure.

In an embodiment, the graph illustrated in FIG. 4 represents the input data set, wherein the x-axis represents range bin (in meters(s)) and the y-axis represents time samples (in seconds (s)).

Figure 3:
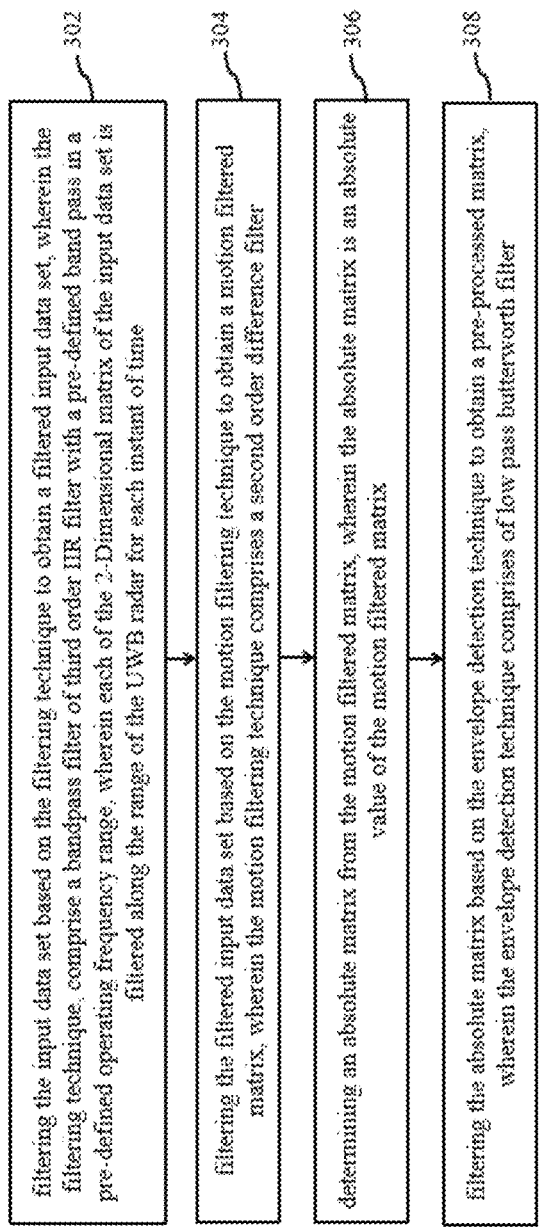
FIG. 3 is a flow diagram illustrating a method for pre-processing the input data set based on a filtering technique, a motion detection technique, and an envelope detection technique for pre-processing the input data set, in accordance with some embodiments of the present disclosure.

According to an embodiment of the disclosure, the system 100 further comprises a pre-processor 204 configured for preprocessing, by the one or more hardware processors, the input data set based on a filtering technique, a motion detection technique, and an envelope detection technique to obtain a pre-processed matrix, wherein the pre-processed matrix comprises of a plurality of range bins for a plurality of instances of range bin time In one embodiment, the method for the pre-processing the input data set based on a filtering technique, a motion detection technique, and an envelope detection technique to obtain a pre-processed matrix is described further with reference to FIG. 3, as described below.

Referring to the FIG. #3, at step (302), the method (300) includes filtering the input data set based on the filtering technique to obtain a filtered input data set, wherein the filtering technique, comprise a bandpass filter of third order IIR filter with a pre-defined band pass in a pre-defined operating frequency range, wherein each of the 2-Dimensional matrix of the input data set is filtered along the range of the one or more UWB radar for each instant of time.

In an embodiment, the input data set is filtered using a bandpass filter of 3rd order IIR filter with band pass in pre-defined operating frequency range of 3.1 GHz to 4.8 GHz along the range axis.

Figure 5:
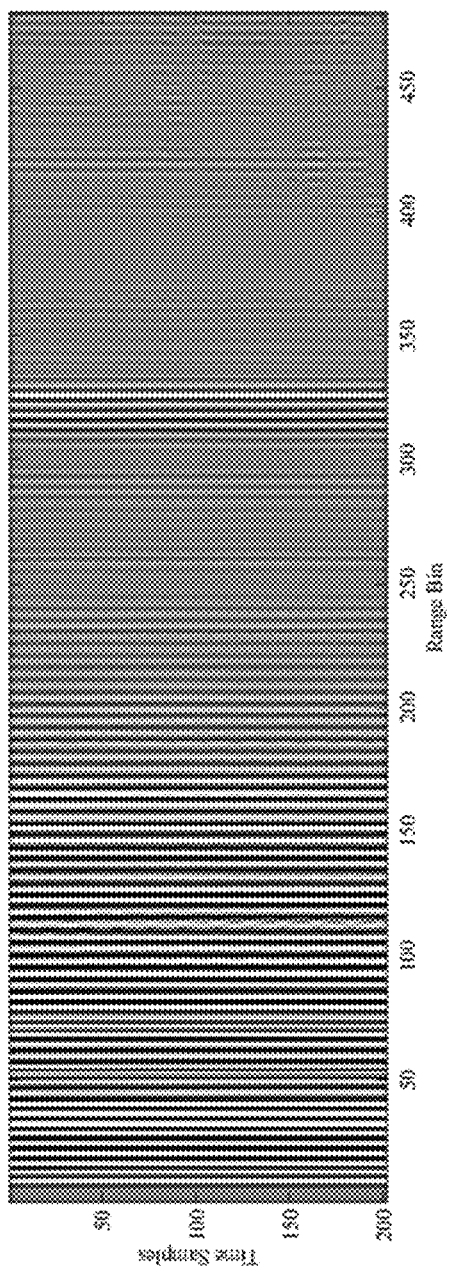
FIG. 5 illustrates a graph indicative of variation of an input data set during preprocessing of the input data set associated with determination of cardiopulmonary signals for multi-persons based on the filtering technique, in accordance with some embodiments of the present disclosure.

In an example, the graph illustrated in FIG. 5 represents the filtered input data set, wherein the x-axis represents range bin (in m) and the y-axis represents time samples (in ms).

At the next step (304), the method (300) includes filtering the filtered input data set based on the motion filtering technique to obtain a motion filtered matrix, wherein the motion filtering technique comprises a second order difference filter.

Figure 6:
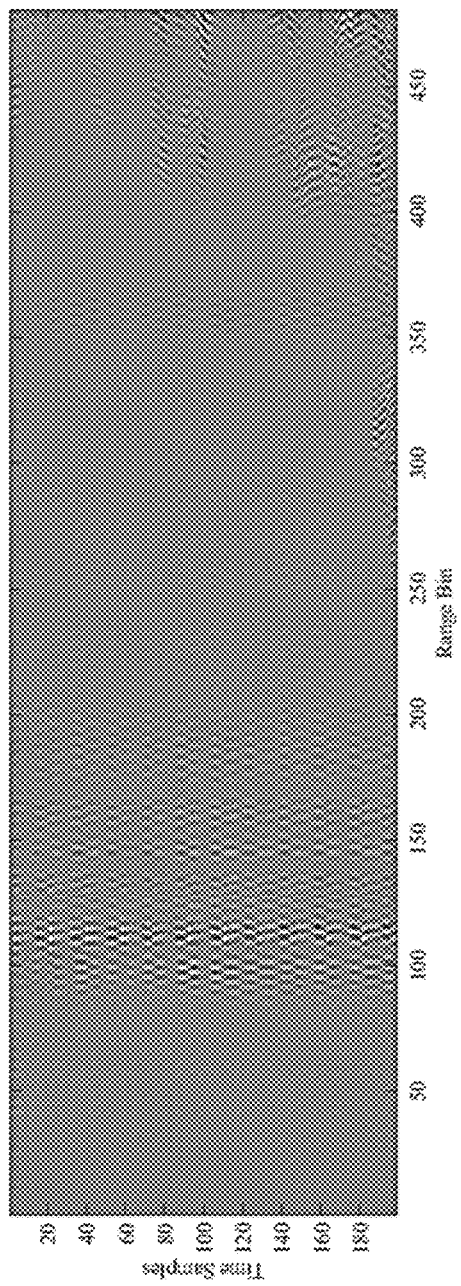
FIG. 6 illustrates a graph indicative of variation of an input data set during preprocessing the input data set based on the motion detection technique, in accordance with some embodiments of the present disclosure.

In an example, the graph illustrated in FIG. 6 represents the motion filtered matrix, wherein the x-axis represents range bin (in m) and the y-axis represents time samples (in ms).

At the next step (306), the method (300) includes determining an absolute matrix from the motion filtered matrix, wherein the absolute matrix is an absolute value of the motion filtered matrix.

At the next step (308), the method (300) includes filtering the absolute matrix based on the envelope detection technique to obtain a pre-processed matrix, wherein the envelope detection technique comprises of low pass butterworth filter.

Figure 7:
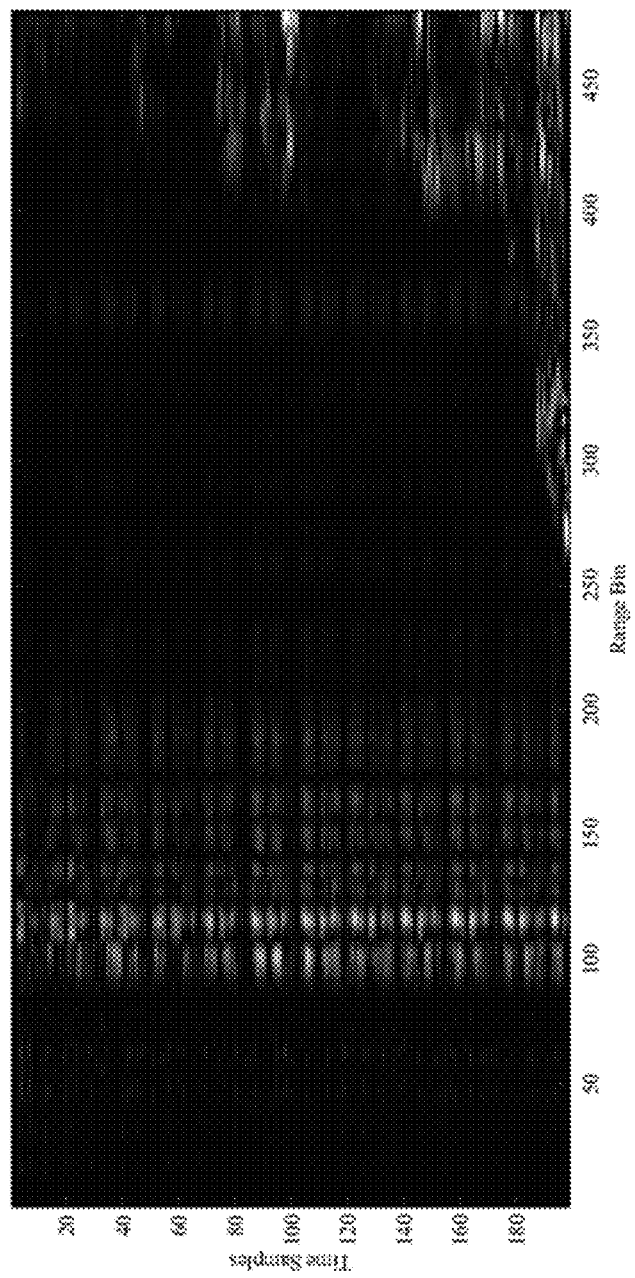
FIG. 7 illustrates a graph indicative of variation of an input data set during preprocessing the input data set based on the envelope detection technique, in accordance with some embodiments of the present disclosure.

In an example, the graph illustrated in the FIG. 7 represents the pre-processed matrix (obtained after envelope detection), wherein the x-axis represents range bin (in m) and the y-axis represents time samples (in ms).

According to an embodiment of the disclosure, the system 100 for determination of cardiopulmonary signals for multi-persons using in-body signals obtained by the one or more UWB radar further comprises a multiple person module 206 that further comprises a multi-person identifier 208, a girth identifier 210, an orientation identifier 212. The functions for each module within the multiple person module 206 are explained in the sections below.

According to an embodiment of the disclosure, the system 100 for determination of cardiopulmonary signals for multi-persons using in-body signals obtained by the one or more UWB radar further comprises the multi-person identifier 208 and the girth identifier 210 within the multiple person module 206 of the system 100 for determination of cardiopulmonary signals for multi-persons using in-body signals obtained by the one or more UWB radar.

The multi-person identifier 208 is configured for identifying, by the one or more hardware processors, a plurality of persons in the vicinity of the one or more UWB radar and the girth identifier 210 is configured for identifying a girth for each of the person of the plurality of persons using the pre-processed matrix based on a peak identification technique, wherein the girth of the each person comprises of an entry point and an exit point, where the entry point and the exit point are indicative of a category of the person's body type.

Figure 8:
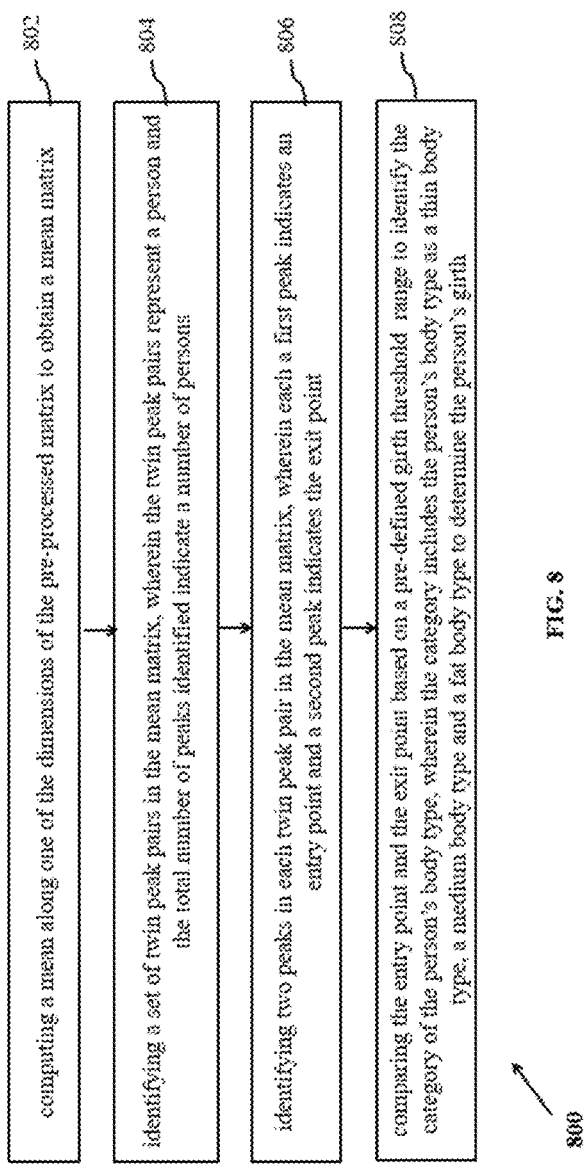
FIG. 8 is a flow diagram illustrating a method for identification of the number of persons and a girth for each person of the plurality of persons (multi-person), in accordance with some embodiments of the present disclosure.
Figure 9:
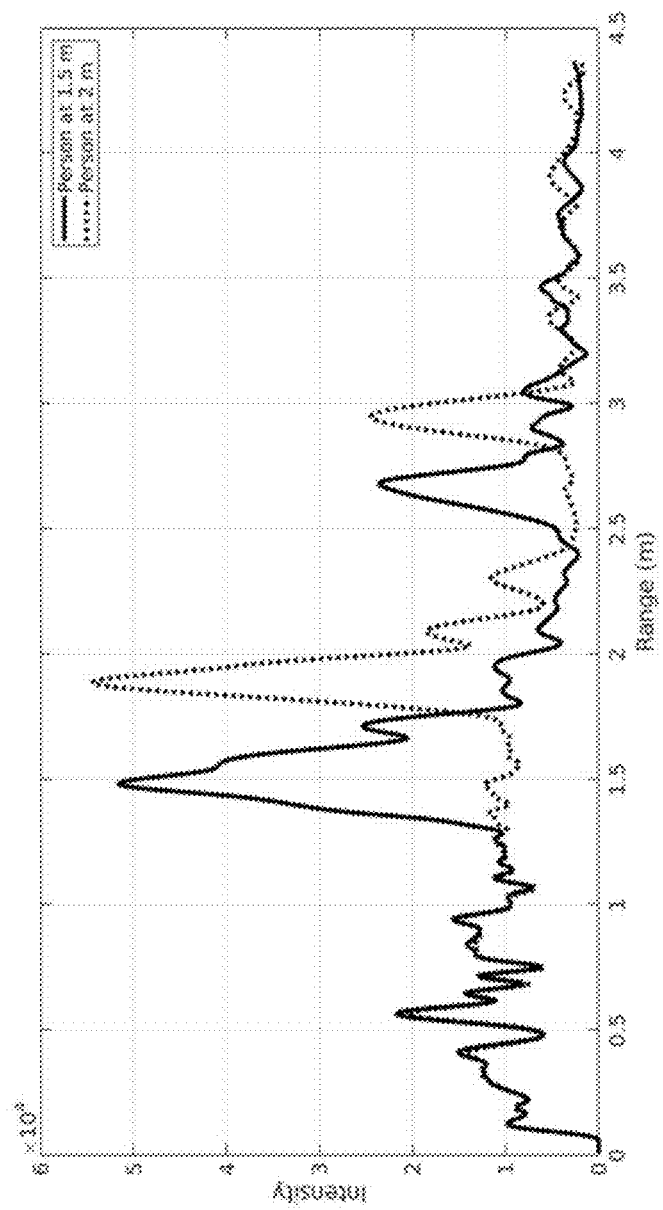
FIG. 9 illustrates a graph indicative of identification of the number of persons (multi-person), in accordance with some embodiments of the present disclosure.

In one embodiment, the method (800) for identification of the number of persons and the girth for each person of the plurality of persons based on the peak identification technique is described further with reference to FIG. 8, as described below:

Referring to FIG. 8, at step (802), the method (800) includes computing a mean along one of the dimensions of the pre-processed matrix to obtain a mean matrix.

In an embodiment, consider a use case example of a pre-processed matrix A with dimension M×N. A mean along one of the dimensions (say N) is computed for all M elements to obtain a mean matrix (B) with the dimension 1×N.

At the next step (804), the method (800) includes identifying a set of twin peak pairs in the mean matrix, wherein the twin peak pairs represent a person and the total number of peaks identified indicate a total number of persons.

In an embodiment, a sharp change or peak is observed and is visible in the mean matrix, wherein each twin peak pairs in the mean matrix indicates a person. Hence the total number of twin peak pairs identified indicates the total number of persons. In an embodiment, in the graph illustrated in the FIG. 9, the twin peak pairs can be identified at 1.5 m and 2 m, hence identifying two persons.

At the next step (806), the method (800) includes identifying a first peak and a second peak in each twin peak pair in the mean matrix, wherein each the first peak indicates an entry point and the second peak indicates the exit point For each person identified, a pair of peaks is observed in the mean matrix, wherein the pair of peaks correspond to a location where the UWB radar signal enter the person's body and a location wherein the UWB radar signal exit the person's body. The location where the UWB radar signal (the first peak) enters the person's body is identified as the entry point and location where the UWB radar signal (the second peak) exits the person's body is identified as the exit point.

Figure 10:
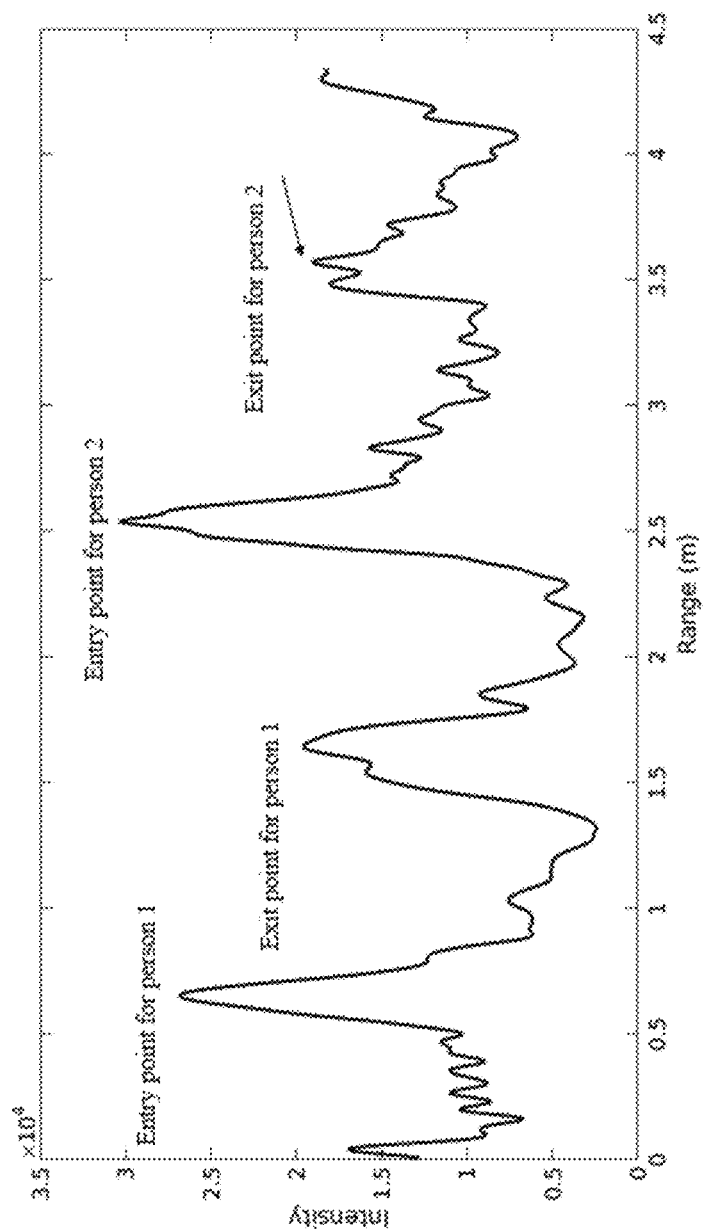
FIG. 10 illustrates a graph indicative of identification of the girth for each person of the plurality of persons, in accordance with some embodiments of the present disclosure.

In an embodiment, in the graph illustrated in the FIG. 10, two persons can be identified, wherein an entry point for a person 1 is at 0.6 m and an exit point for the person 1 is at 1.6 m, while an entry point for a person 2 is at 2.5 m and an exit point for the person 2 is at 3.5 m.

At the next step (808), the method (800) includes comparing the entry point and the exit point based on a pre-defined girth threshold range to identify the category of the person's body type, wherein the category includes the person's body type as a thin body type, a medium body type and a fat body type to determine the person's girth.

In an embodiment, the pre-defined girth threshold range is pre-defined as for less than 1 for the thin body type, between 1-1.75 for the medium body type and more than 1.75 for the fat body. A difference value between the entry point and the exit point is computed to be compared with the pre-defined girth threshold range to obtain the category of the person's body type.

According to an embodiment of the disclosure, the system 100 for determination of cardiopulmonary signals for multi-persons using in-body signals obtained by the one or more UWB radar further comprises the orientation identifier 212 within the multiple person module 206 of the system 100 for determination of cardiopulmonary signals for multi-persons using in-body signals obtained by One or more UWB radar. The orientation identifier 212 is configured for identifying, by the one or more hardware processors, an orientation for each of the identified person of the plurality of persons using the pre-processed matrix based on a plurality of comparison techniques. The orientation is indicative of the orientation of the identified person with respect to the one or more UWB radar, wherein the plurality of comparison techniques comprises an intensity comparison technique and a spectral flatness comparison technique.

In an embodiment, the orientation includes a front facing position of the identified person with respect to the one or more UWB radar, a back facing position of the identified person with respect to the one or more UWB radar and a side facing position of the identified person with respect to the one or more UWB radar.

Figure 11:
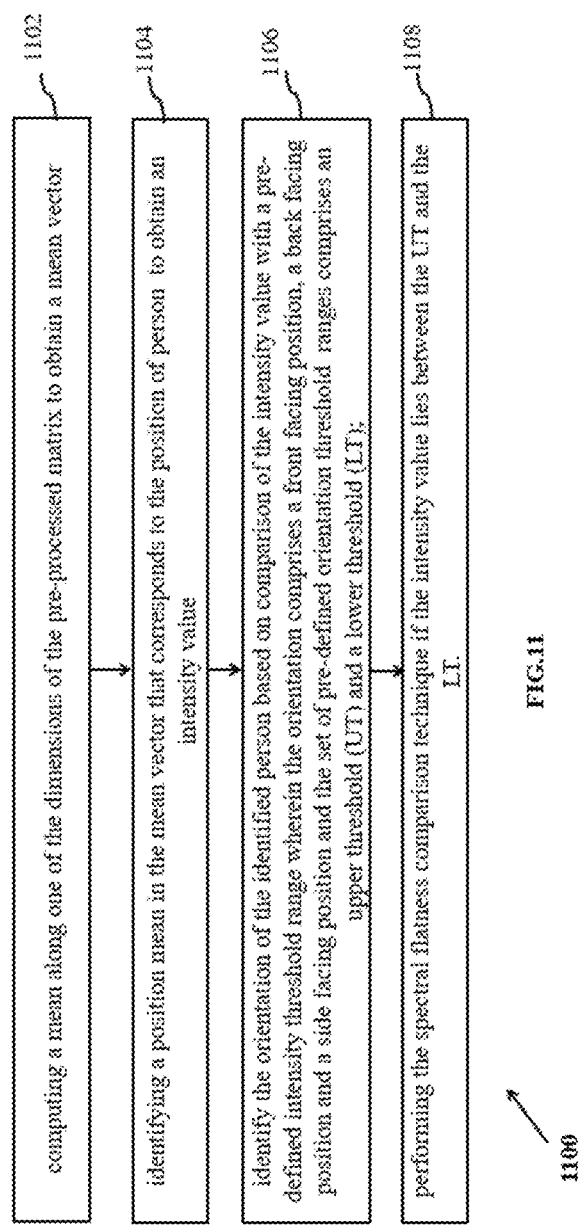
FIG. 11 is a flow diagram illustrating a method for identification of the orientation of the plurality of persons based on the intensity comparison technique, in accordance with some embodiments of the present disclosure.

In one embodiment, the method (1100) for identification of the orientation based on the intensity comparison technique is described further with reference to the FIG. 11, as described below:

Referring to the FIG. 11, at step (1102), the method (1100) includes computing a mean along one of the dimensions of the pre-processed matrix to obtain a mean vector.

In an embodiment, consider a use case example of a pre-processed matrix A with dimension M×N. A mean along one of the dimensions (say N) is computed for all M elements to obtain a mean matrix (B) with the dimension 1×N.

At the next step (1104), the method (1100) includes identifying a position mean in the mean vector that corresponds to the position of person to obtain an intensity value.

At the next step (1106), the method (1100) includes identifying the orientation of the identified person based on comparison of the intensity value with a pre-defined intensity threshold range wherein the orientation comprises a front facing position, a back facing position and a side facing position and the set of pre-defined orientation threshold ranges comprises an upper threshold (UT) and a lower threshold (LT).

In an embodiment, for the set of pre-defined orientation threshold ranges a use case example defines the upper threshold (UT) at 110 decibel (dB) and the lower threshold (LT) at 90 dB. Hence for an intensity value above UT is identified as front facing position and an intensity value below LT is identified as a back facing position.

At the next step (1108), the method (1100) includes performing the spectral flatness comparison technique if the intensity value lies between the UT and the LT.

Figure 12:
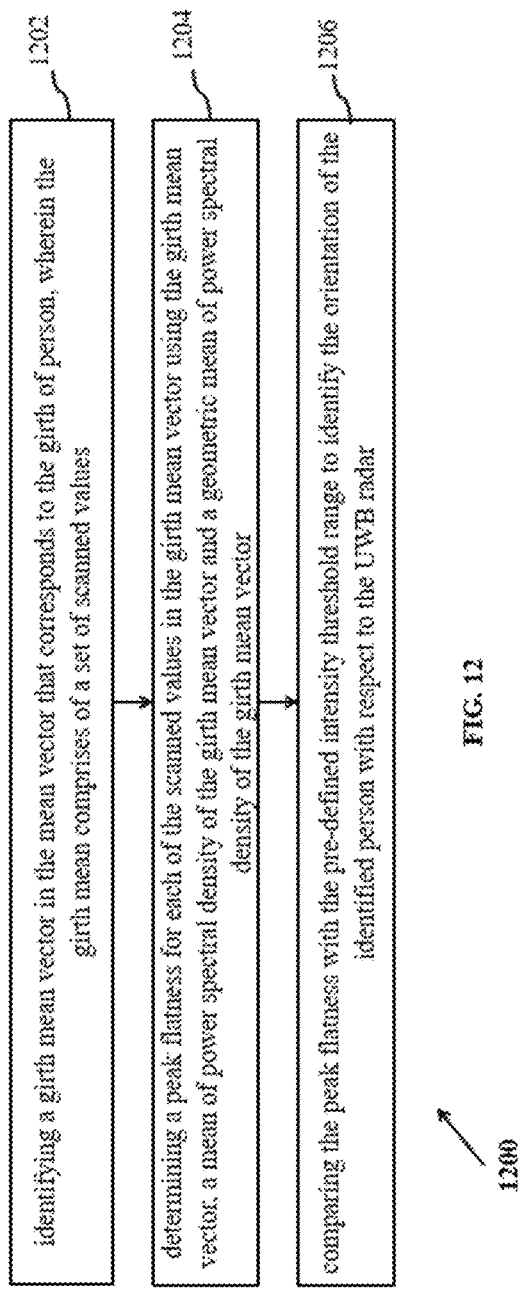
FIG. 12 is a flow diagram illustrating a method for identification of the orientation of the plurality of persons based on the spectral flatness comparison technique, in accordance with some embodiments of the present disclosure.

In one embodiment, the method for identification of the orientation based on the spectral flatness comparison technique(1200) comprises is described further with reference to FIG. 12, as described below:

Referring to FIG. 12, at step (1202), the method (1200) identifying a girth mean vector in the mean vector that corresponds to the girth of person, wherein the girth mean comprises of a set of scanned values.

At the next step (1206), the method (1200) includes determining a peak flatness for each of the scanned values in the girth mean vector using the girth mean vector, a mean of power spectral density of the girth mean vector and a geometric mean of power spectral density of the girth mean vector. The peak flatness is expressed as shown below:

$$\text{peak flatness} = \frac{\sqrt{P}}{\text{mean}(P)} \quad (1)$$

Where,

P is the power spectral density of the girth mean vector and a geometric mean of power spectral density of the girth mean vector.

At the next step (1208), the method (1200) includes comparing the peak flatness with the pre-defined intensity threshold range to identify the orientation of the identified person with respect to the one or more UWB radar.

Figure 13:
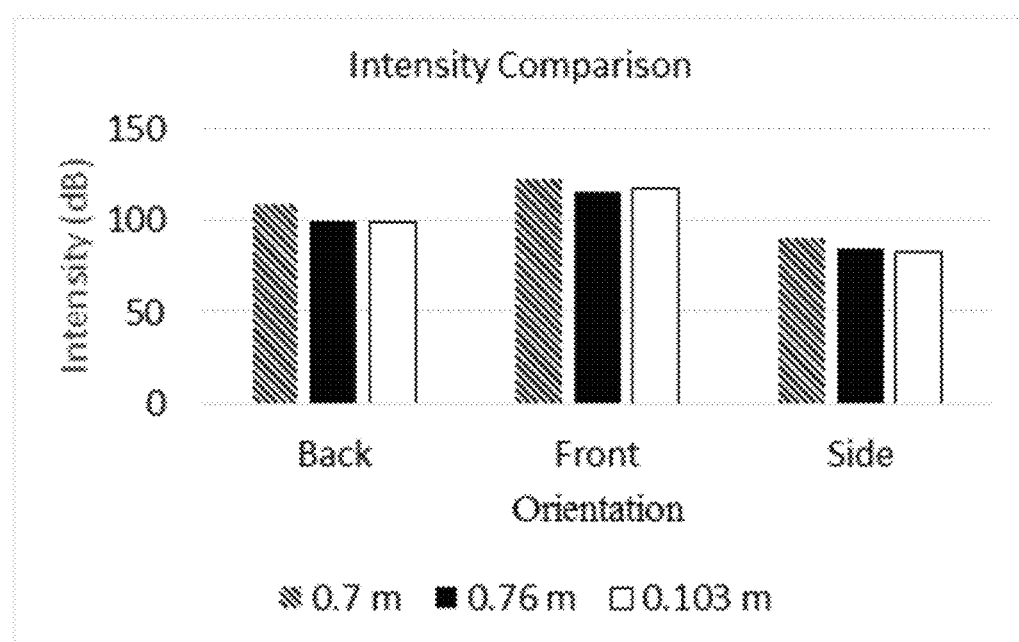
FIG. 13 illustrates a graph for intensity comparison with a pre-defined intensity threshold range to identify the orientation of the identified person with respect to the One or more UWB radar, in accordance with some embodiments of the present disclosure.
Figure 14:
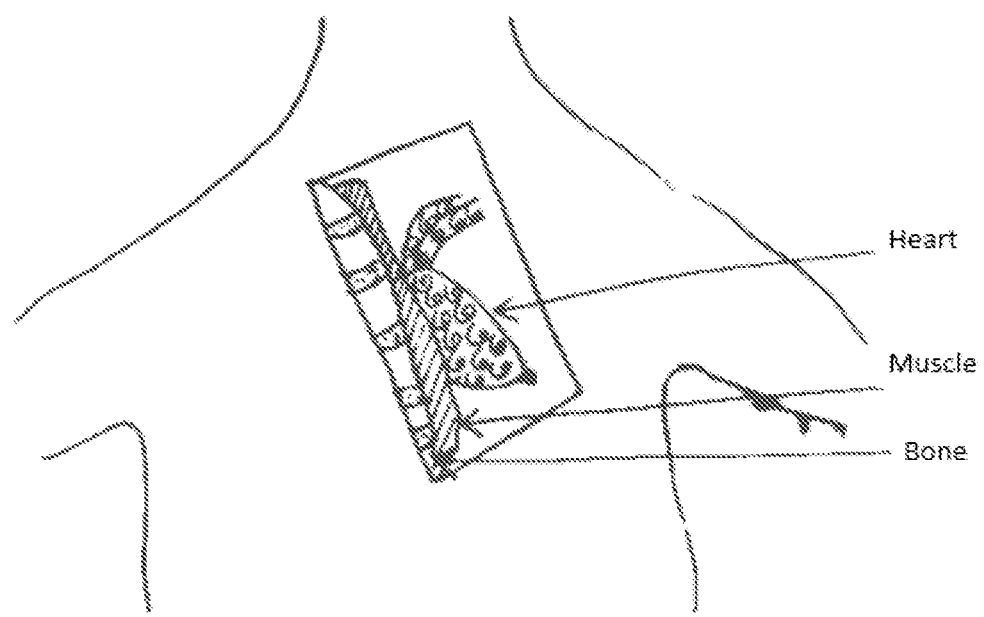
FIG. 14 illustrates a use case example block diagram of the anatomy of a human body for determination of cardiopulmonary signals of multi-persons according to some embodiments of the present disclosure.

In an embodiment, FIG. 13 illustrates a graph for intensity comparison with a pre-defined intensity threshold range to identify the orientation of the identified person with respect to the one or more UWB radar, wherein the x-axis indicates orientation and the y-axis indicates the intensity.

According to an embodiment of the disclosure, the system 100 further comprises the chest wall distance module 216 within the in-body signal analyzer module 214 of the system 100. The chest wall distance module 216 is configured for determining, by the one or more hardware processors, a chest wall distance for each of the identified person of the plurality of persons using the pre-processed matrix based on the peak identification technique, wherein the chest wall distance is indicative of distance between the one or more UWB radar and each the identified person's chest wall.

In an embodiment, the determination chest wall distance using the pre-processed matrix based on the peak identification technique, comprises of identification of a plurality of peaks from the plurality of range bins of the pre-processed matrix, wherein a peak that is identified first among the plurality of peaks is indicative of the chest wall distance.

According to an embodiment of the disclosure, the system 100 further comprises the breathing rate module 218 within the in-body signal analyzer module 214 of the system 100. The breathing rate module 218 is configured for determining, by the one or more hardware processors, a breathing rate for each of the identified person of the plurality of persons using the pre-processed matrix and the chest wall distance based on a plurality of auto-correlation technique, wherein the plurality of auto-correlation techniques are implemented on a set of time series of the range bins extracted from the pre-processed matrix using the chest wall distance In an embodiment, the auto-correlation techniques performed the set of time series of the range bins (s(t) for time t and $k^{th}$ time sample, can be expressed as shown below:

$$\text{Auto} - \text{correlation} = \frac{\text{Co} - \text{variance } (s(t) + (s(t+k)))}{\sqrt{\text{Variance}(s(t), \text{Variance}(s(t+k))}} \quad (2)$$

For N number of samples,
Where, $$\text{Co} - \text{variance}(s(t), s(t+k)) = \frac{\sum (s(t) - \text{mean}(s(t)) \times (s(t+k) - \text{mean}(s(t+k))}{N} \quad (3)$$

$$\text{Variance}(s(t)) = \frac{\sum (s(t) - \text{mean}(s(t)))^2}{N-1} \quad (4)$$

$$\text{Variance}(s(t+k)) = \frac{\sum (s(t+k) - \text{mean}(s(t+k)))^2}{N-1} \quad (5)$$

According to an embodiment of the disclosure, the system 100 further comprises the heart wall distance module 220 within the in-body signal analyzer module 214 of the system 100. The heart wall distance module 220 is configured for a heart wall distance for each of the identified person of the plurality of persons based on a heart wall distance determination technique. The heart wall distance is indicative of distance between each of the identified person's chest wall and each of the identified person's heart wall and the heart wall distance is determined using a set of pre-defined dielectric constant of a plurality of biological tissues, a set of pre-defined wall values of the plurality of biological tissues, a pre-defined scaling factor for each of the biological tissue The heart wall distance module 220 is further configured for identifying a heart wall range bin for each of the identified person of the plurality of persons based on a heart wall distance determination technique. The heart wall range bin is indicative of a number of the range bin between each of the identified person's heart wall and the one or more UWB radar and the heart wall range bin is determined using the heart wall distance, the chest wall distance and a pre-determined range resolution of the one or more UWB radar In an embodiment, the heart wall distance determination technique comprises of determination of the heart wall distance and the heart wall range bin, which can be expressed as shown below:

$$D = \alpha_1 W_1 \sqrt{\varepsilon_1} + \alpha_2 W_2 \sqrt{\varepsilon_2} + \ldots + \alpha_n W_n \sqrt{\varepsilon_n}. \qquad (6)$$

wherein
D is the heart wall distance
W is the biological tissue
$\alpha$ is a pre-defined scaling factor for each of the biological tissue
$\varepsilon$ dielectric constant of the biological tissue
n represents a "$n^{th}$" biological tissue $$B_{HR} = \text{floor}\left[\frac{D}{Resol_{range}}\right] \qquad (7)$$

Wherein
$B_{HR}$ is the heart wall range bin
D is the heart wall distance
$Resol_{range}$ is the range resolution of the UWB radar
$B_{BR}$ is the chest wall distance Further for determination of the heart wall range bin, anatomy of thoracic cavity of a human is considered. The anatomy of the thoracic cavity of a human is complex and a use case example block diagram of the anatomy of a human body is illustrated in FIG. 13, according to some embodiments of the present disclosure when UWB radar signals/Electro-Magnetic waves enter a human body, the effective width gets multiplied by the dielectric constant of the material or the biological tissue that they pass through. Hence considering number of biological tissues as n=3 wherein the biological tissues considered are bones, muscle tissue and heart wall, a normal person has the depth of bones to be 0.6 cm, muscle tissue to be 2 cm heart wall of 0.25 cm. Considering the values defined, the heart wall distance and the heart wall range bin is determined as shown below:

Using equation (6)

$$D = \alpha_1 W_1 \sqrt{\varepsilon_1} + \alpha_2 W_2 \sqrt{\varepsilon_2} + \ldots + \alpha_n W_n \sqrt{\varepsilon_n}$$

$$D = 0.6\sqrt{20} + 2\sqrt{54} + \ldots + 0.25\sqrt{54}$$

$$D = 0.192$$

Using equation (7)

$$B_{HR} = \text{floor}\left[\frac{D}{Resol_{range}}\right]$$

$$B_{HR} = \text{floor}\left[\frac{0.192}{0.0091}\right]$$

$$B_{HR} = 21 \text{ bins}$$

According to an embodiment of the disclosure, the system 100 further comprises a heart rate module 222 within the in-body signal analyzer module 214 of the system 100. The heart rate module 222 is configured for determining, by the one or more hardware processors, a heart rate for each of the identified person of the plurality of persons using the pre-processed matrix, the heart wall distance and a pre-determined time resolution of the one or more UWB radar based on a heart rate determination technique, heart rate determination technique comprises of a frequency domain technique and a harmonic removal technique.

Figure 15:
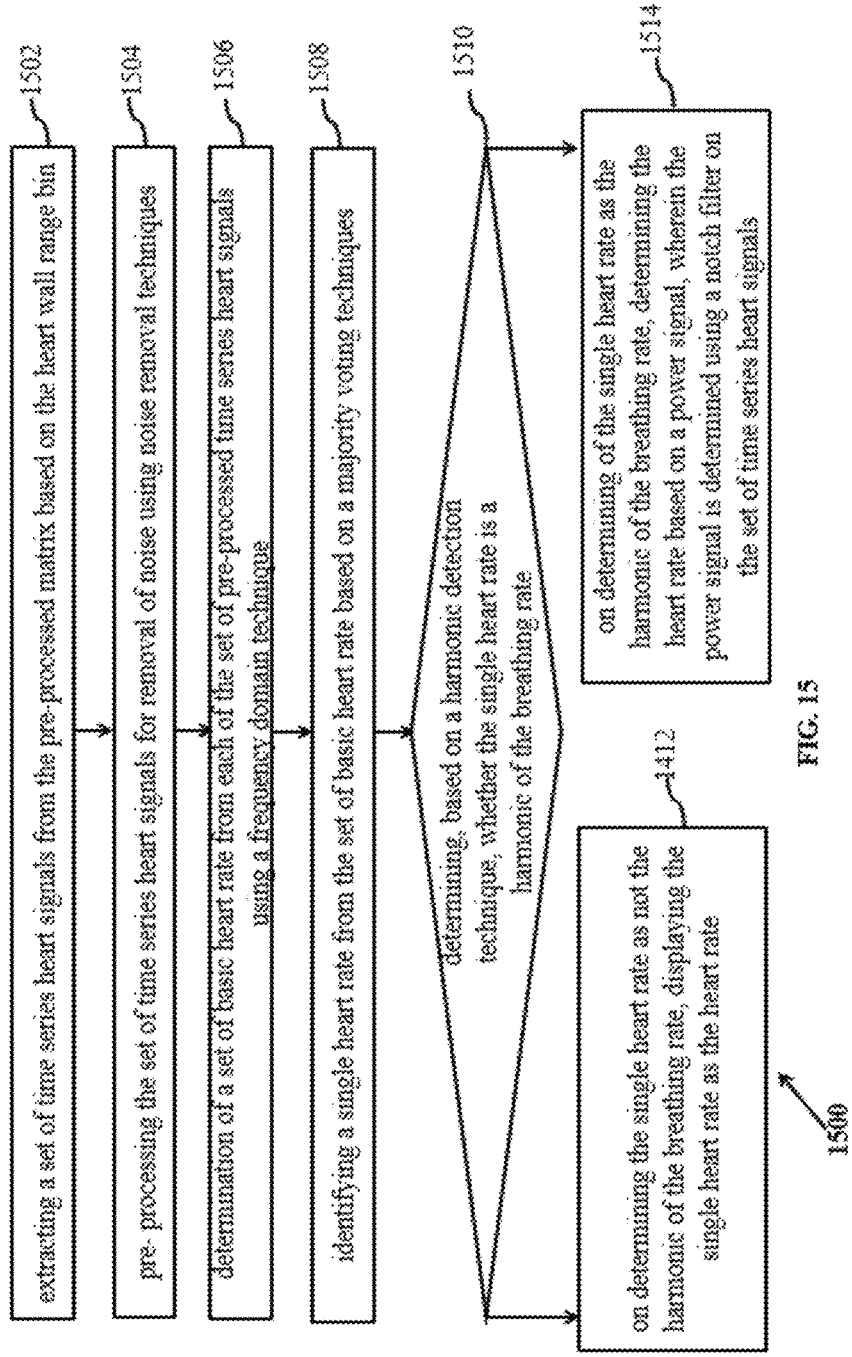
FIG. 15 is a flow diagram illustrating a method for determining a heart rate for each of the identified person of the plurality of persons, in accordance with some embodiments of the present disclosure.

In one embodiment, the method (1500) for the heart rate determination technique is described further with reference to the FIG. 15, as described below:

Referring to the FIG. 15, at step (1502), the method (1500) includes extracting a set of time series heart signals from the pre-processed matrix based on the heart wall range bin.

At the next step (1504), the method (1500) includes pre-processing the set of time series heart signals for removal of noise using noise removal techniques. In an embodiment, the noise removal techniques include of several steps that include mean removal, normalization, standardization and standard deviation as shown below; The mean removal for a time series heart signals s(t) is expressed as shown below:

$$S_1(t) = s(t) - \text{mean}(s(t)) \qquad (8)$$

The normalization process is expressed as shown below:

$$S_2(t) = \frac{(s_1(t) - \min(s_1(t)))}{\max(s_1(t)) - \min(s_1(t))} \qquad (9)$$

The standardization process is expressed as shown below:

$$S_3(t) = \frac{s_2(t) - \text{mean}(s_2(t))}{\text{standard deviation}(s_2(t))} \qquad (10)$$

Where standard deviation of $s_2(t)$ of N samples is as shown below:

$$\text{Standard Deviation } (s_2(t)) = \sqrt{\frac{\sum (s_2(t) - \text{mean}(s_2(t)))^2}{N}} \qquad (11)$$

At the next step (1506), the method (1500) includes determination of a set of basic heart rate from each of the set of pre-processed time series heart signals using a frequency domain technique. In an embodiment, the frequency domain technique comprises of Fast Fourier transform algorithm, Pwelch algorithm, wavelet transforms, Laplace Transforms.

At the next step (1508), the method (1500) includes identifying a single heart rate from the set of basic heart rate based on a majority voting technique. In an embodiment, the majority voting techniques comprises of Boyer Moore Majority Voting Algorithm, Moore's Voting Algorithm.

At the next step (1510), the method (1500) includes determining, based on a harmonic detection technique, whether the single heart rate is a harmonic of the breathing rate.

At the next step (1512 or 1514), the method (1500) includes performing, upon determining, one of:
On determining the single heart rate as not the harmonic of the breathing rate, displaying the single heart rate as the heart rate. (1512)

On determining of the single heart rate as the harmonic of the breathing rate, determining the heart rate based on a power signal, wherein the power signal is determined using a notch filter on the set of time series heart signals. (1514)

Figure 16:
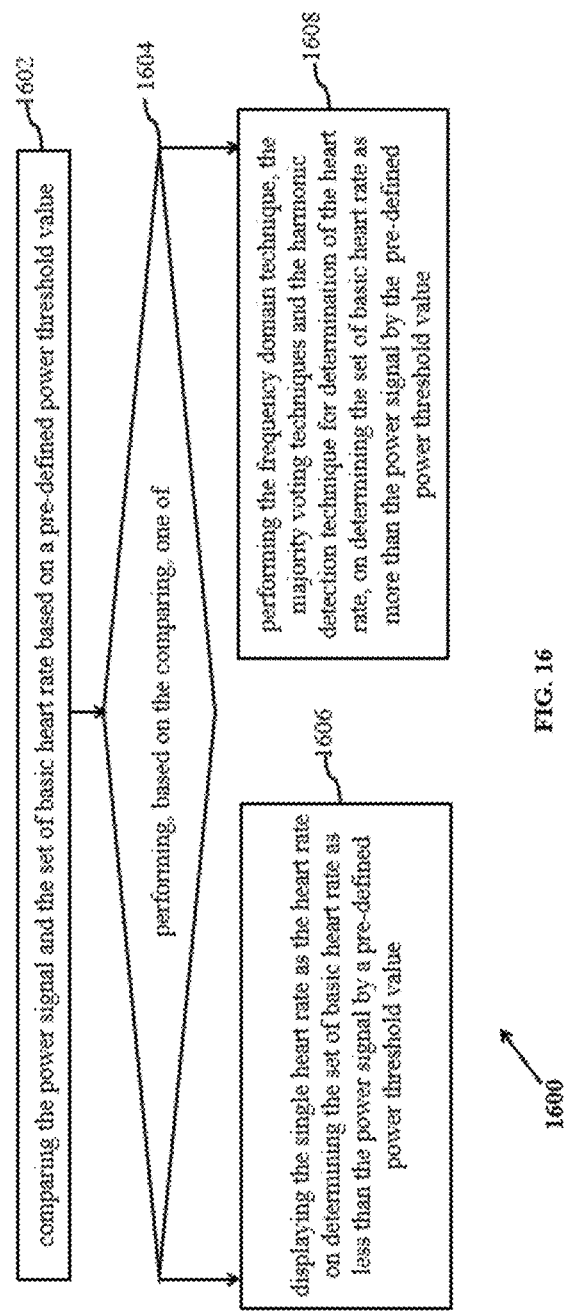
FIG. 16 is a flow diagram illustrating a method for determining the heart rate based on the power signal, in accordance with some embodiments of the present disclosure.

In one embodiment, the method for comparing the power signal and the set of basic heart rate based on a pre-defined power threshold value is described further with reference to the FIG. 16, as described below:

Referring to the FIG. 16, at step (1602), the method (1600) includes comparing the power signal and the set of basic heart rate based on a pre-defined power threshold value. In an embodiment, the power of the time series heart signals s(t), for a duration of T time units can be expressed as shown below:

$$\text{Power} = \frac{1}{T}\int_0^T |s(t)|^2 dt \qquad (12)$$

In an embodiment, the pre-defined power threshold value is defined as 30.

At the next step (1604), the method (1600) includes performing, based on the comparing, one of:
  displaying the single heart rate as the heart rate on determining the set of basic heart rate as less than the power signal by a pre-defined power threshold value; (1606)
  performing the frequency domain technique, the majority voting techniques and the harmonic detection technique for determination of the heart rate, on determining the set of basic heart rate as more than the power signal by the pre-defined power threshold value. (1608)

According to an embodiment of the disclosure, the system 100 further comprises a display module 224 configured for displaying the determined heart rate and the determined breathing rate, wherein the determined heart rate and the determined breathing rate is indicative of the cardiopulmonary signals.

In an embodiment, the cardiopulmonary signals are continuously determined to make the system 100 for a continuous cardiopulmonary signals monitoring platform, wherein the cardiopulmonary signals at an instance of time is displayed on the display module 224. The continuous determination of cardiopulmonary signals enables continuous monitoring of health status of the person/human.

The various modules of the system 100 for determination of cardiopulmonary signals for multi-persons using in-body signals obtained by Ultra-wide band (UWB) radar are implemented as at least one of a logically self-contained part of a software program, a self-contained hardware component, and/or, a self-contained hardware component with a logically self-contained part of a software program embedded into each of the hardware component that when executed perform the above method described herein.

Figure 17A:
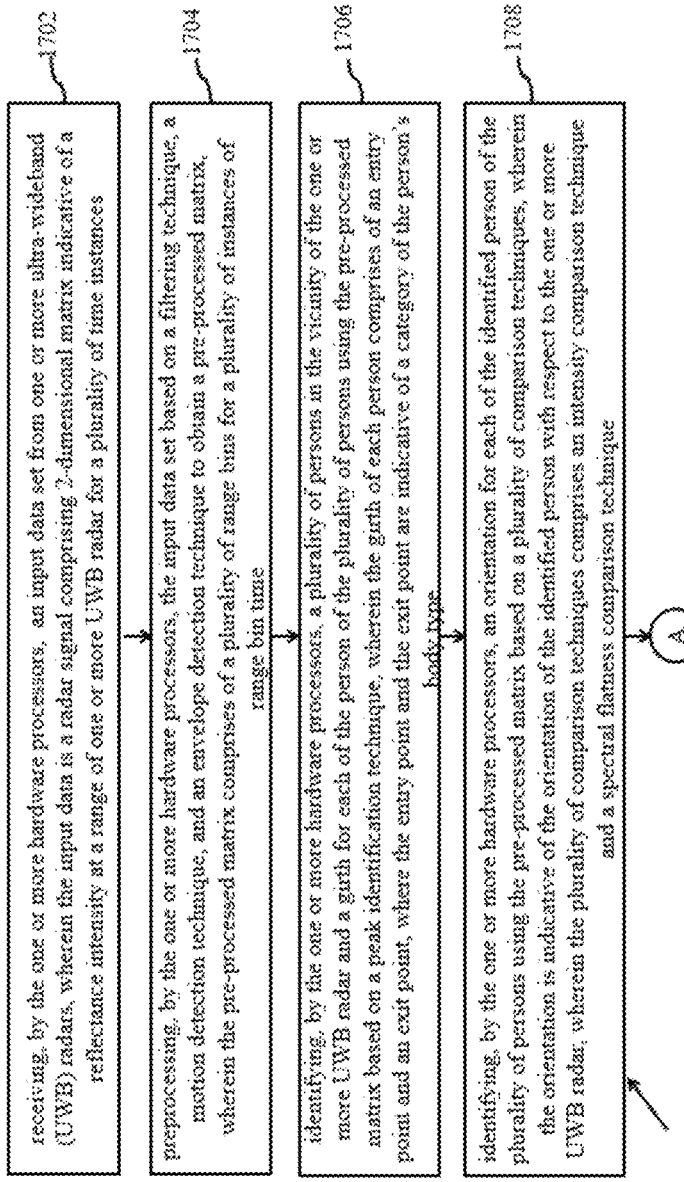
FIG. 17A, FIG. 17B and FIG. 17C is a flow diagram illustrating a method for determination of cardiopulmonary signals for multi-persons using in-body signals obtained by One or more UWB radar in accordance with some embodiments of the present disclosure.
Figure 17B:
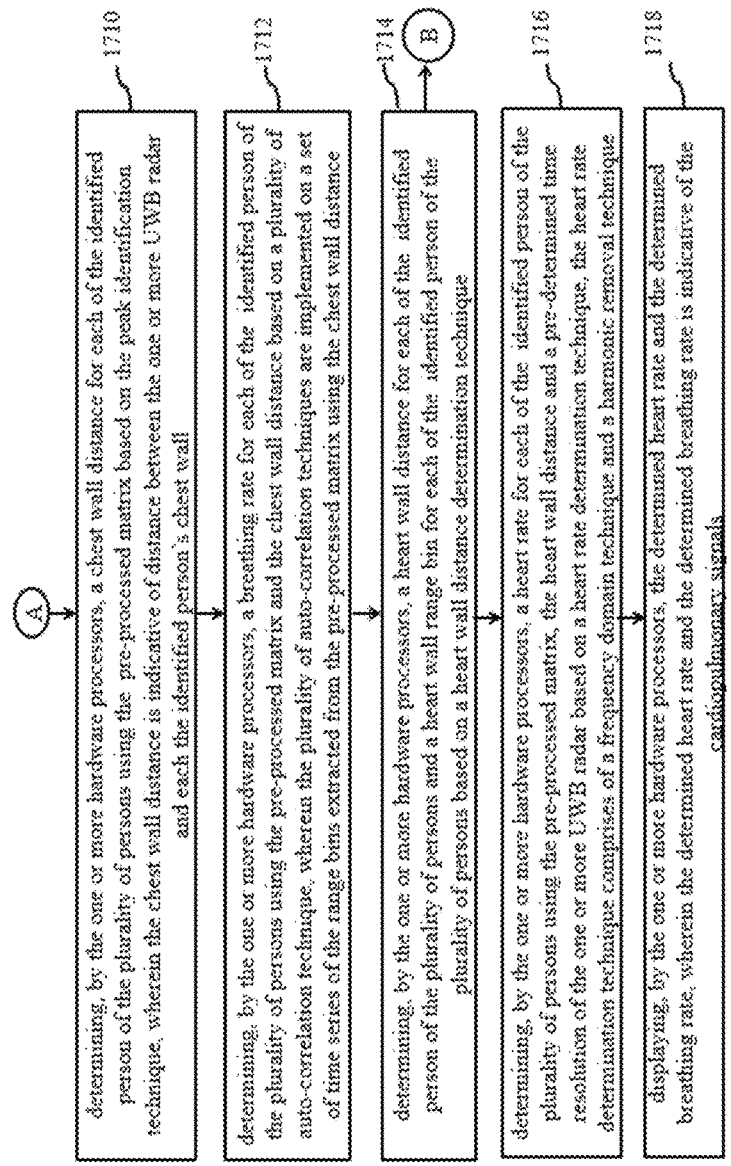
Figure 17C:
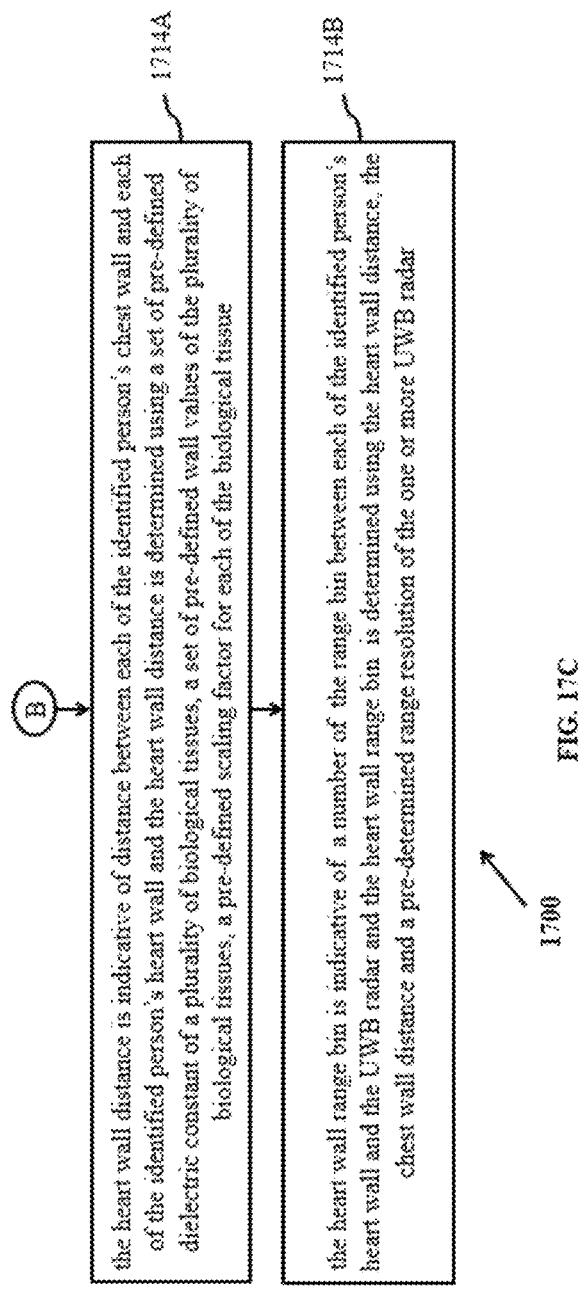

Functions of the components of the system 100 are explained in conjunction with functional modules of the system 100 stored in the memory 102 and further explained in conjunction with flow diagram of FIG. 17A, FIG. 17B and FIG. 17C. The FIG. 17A, FIG. 17B and FIG. 17C, with reference to FIG. 1 and FIG. 2, is an exemplary flow diagram illustrating a method (1700) for using the system 100 of FIG. 1 according to an embodiment of the present disclosure.

The steps of the method of the present disclosure will now be explained with reference to the components of the system 100 for determination of cardiopulmonary signals for multi-persons using in-body signals obtained by the one or more Ultra-wide band (UWB) radar system and the modules (202-224) as depicted in FIG. 2 and the flow diagrams as depicted in FIG. 17A, FIG. 17B and FIG. 17C. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously and is described further with reference to the FIG. 17A, FIG. 17B and FIG. 17C as described below:

Referring to the FIG. 17, at step 1702 of the method (1700) includes receiving, by the one or more hardware processors, an input data set from one or more ultra-wideband (UWB) radars, wherein the input data is a UWB radar signal comprising 2-dimensional matrix indicative of a reflectance intensity at a range of the One or more UWB radar for a plurality of time instances At step 1704 of the method (1700), includes preprocessing, by the one or more hardware processors, the input data set based on a filtering technique, a motion detection technique, and an envelope detection technique to obtain a pre-processed matrix, wherein the pre-processed matrix comprises of a plurality of range bins for a plurality of instances of range bin time.

In an embodiment, the pre-processing method comprises several steps that includes filtering the input data set based on the filtering technique to obtain a filtered input data set, wherein the filtering technique, comprise a bandpass filter of third order IIR filter with a pre-defined band pass in a pre-defined operating frequency range, wherein each of the 2-Dimensional matrix of the input data set is filtered along the range of the one or more UWB radar for each instant of time. The pre-processing method further comprises filtering the filtered input data set based on the motion filtering technique to obtain a motion filtered matrix, wherein the motion filtering technique comprises a second order difference filter. The pre-processing method further comprises determining an absolute matrix from the motion filtered matrix, wherein the absolute matrix is an absolute value of the motion filtered matrix. The pre-processing method further comprises filtering the absolute matrix based on the envelope detection technique to obtain a pre-processed matrix, wherein the envelope detection technique comprises of low pass butterworth filter.

At step 1706 of the method (1700), includes identifying, by the one or more hardware processors, a plurality of persons in the vicinity of the one or more UWB radar and a girth for each of the person of the plurality of persons using the pre-processed matrix based on a peak identification technique, wherein the girth of the each person comprises of an entry point and an exit point, where the entry point and the exit point are indicative of a category of the person's body type In an embodiment, the identification of the number of persons and the girth for each person of the plurality of persons comprises of several steps that include computing a mean along one of the dimensions of the pre-processed matrix to obtain a mean matrix. The identification of the number of persons and the girth for each person of the plurality of persons further includes identifying a set of twin peak pairs in the mean matrix, wherein the twin peak pairs represent a person and the total number of peaks identified indicate a number of persons. The identification of the number of persons and the girth for each person of the plurality of persons further includes identifying a first peak and a second peak in each twin peak pair in the mean matrix, wherein each a first peak indicates an entry point and a second peak indicates the exit point. The identification of the number of persons and the girth for each person of the plurality of persons further includes comparing the entry point and the exit point based on a pre-defined girth threshold range to identify the category of the person's body type, wherein the category includes the person's body type as a thin body type, a medium body type and a fat body type to determine the person's girth.

At step 1708 of the method (1700), includes identifying, by the one or more hardware processors, an orientation for each of the identified person of the plurality of persons using the pre-processed matrix based on a plurality of comparison techniques, wherein the orientation is indicative of the orientation of the identified person with respect to the one or more UWB radar, wherein the plurality of comparison techniques comprises an intensity comparison technique and a spectral flatness comparison technique In an embodiment, the orientation includes a front facing position of the identified person with respect to the one or more UWB radar, a back facing position of the identified person with respect to the one or more UWB radar and a side facing position of the identified person with respect to the one or more UWB radar.

In an embodiment, the identification of the orientation based on the intensity comparison technique comprises of several steps that include computing a mean along one of the dimensions of the pre-processed matrix to obtain a mean vector. The intensity comparison technique further includes identifying a position mean in the mean vector that corresponds to the position of person to obtain an intensity value. The intensity comparison technique further includes identify the orientation of the identified person based on comparison of the intensity value with a pre-defined intensity threshold range wherein the orientation comprises a front facing position, a back facing position and a side facing position and the set of pre-defined orientation threshold ranges comprises an upper threshold (UT) and a lower threshold (LT). The intensity comparison technique further includes performing the spectral flatness comparison technique if the intensity value lies between the UT and the LT.

In an embodiment, the identification of the orientation based on the spectral flatness comparison technique comprises of several steps that include identifying a girth mean vector in the mean vector that corresponds to the girth of person, wherein the girth mean comprises of a set of scanned values. The spectral flatness comparison technique further includes determining a peak flatness for each of the scanned values in the girth mean vector using the girth mean vector, a mean of power spectral density of the girth mean vector and a geometric mean of power spectral density of the girth mean vector. The spectral flatness comparison technique further includes comparing the peak flatness with the pre-defined intensity threshold range to identify the orientation of the identified person with respect to the one or more UWB radar.

At step 1710 of the method (1700), includes determining, by the one or more hardware processors, a chest wall distance for each of the identified person of the plurality of persons using the pre-processed matrix based on the peak identification technique, wherein the chest wall distance is indicative of distance between the One or more UWB radar and each the identified person's chest wall In an embodiment, the determination chest wall distance using the pre-processed matrix based on the peak identification technique, comprises of identification of a plurality of peaks from the plurality of range bins of the pre-processed matrix, wherein a peak that is identified first among the plurality of peaks is indicative of the chest wall distance.

At step 1712 of the method (1700), includes determining, by the one or more hardware processors, a breathing rate for each of the identified person of the plurality of persons using the pre-processed matrix and the chest wall distance based on a plurality of auto-correlation technique, wherein the plurality of auto-correlation techniques are implemented on a set of time series of the range bins extracted from the pre-processed matrix using the chest wall distance At step 1714 of the method (1700), includes determining, by the one or more hardware processors, a heart wall distance for each of the identified person of the plurality of persons and a heart wall range bin for each of the identified person of the plurality of persons based on a heart wall distance determination technique.

At step 1714A of the method (1700), the heart wall distance is indicative of distance between each of the identified person's chest wall and each of the identified person's heart wall and the heart wall distance is determined using a set of pre-defined dielectric constant of a plurality of biological tissues, a set of pre-defined wall values of the plurality of biological tissues, a pre-defined scaling factor for each of the biological tissue.

At step 1714B of the method (1700), the heart wall range bin is indicative of a number of the range bin between each of the identified person's heart wall and the one or more UWB radar and the heart wall range bin is determined using the heart wall distance, the chest wall distance and a pre-determined range resolution of the one or more UWB radar In an embodiment, the heart wall distance determination technique comprises of determination of the heart wall distance and the heart wall range bin, which can be expressed as shown below:

$$D = \alpha_1 W_1 \sqrt{\varepsilon_1} + \alpha_2 W_2 \sqrt{\varepsilon_2} + \ldots + \alpha_n W_n \sqrt{\varepsilon_n}$$

wherein
D is the heart wall distance
W is the biological tissue
α is a pre-defined scaling factor for each of the biological tissue
ε dielectric constant of the biological tissue
n represents a "$n^{th}$" biological tissue $$B_{HR} = \text{floor}\left[\frac{D}{Resol_{range}}\right] + B_{BR}$$

Wherein
$B_{HR}$ is the heart wall range bin
D is the heart wall distance
$Resol_{range}$ is the range resolution of One or more UWB radar
$B_{BR}$ is the chest wall distance At step 1716 of the method (1700), includes determining, by the one or more hardware processors, a heart rate for each of the identified person of the plurality of persons using the pre-processed matrix, the heart wall distance and a pre-determined time resolution of the one or more UWB radar based on a heart rate determination technique, heart rate determination technique comprises of a frequency domain technique and a harmonic removal technique In an embodiment, the heart rate determination technique comprises of several steps that includes extracting a set of time series heart signals from the pre-processed matrix based on the heart wall range bin. The heart rate determination technique further comprises pre-processing the set of time series heart signals for removal of noise using noise removal techniques. The heart rate determination technique further comprises determination of a set of basic heart rate from each of the set of pre-processed time series heart signals using a frequency domain technique. The heart rate determination technique further comprises identifying a single heart rate from the set of basic heart rate based on a majority voting technique. The heart rate determination technique further comprises determining, based on a harmonic detection technique, whether the single heart rate is a harmonic of the breathing rate. The heart rate determination technique further comprises performing, upon determining, one of: on determining the single heart rate as not the harmonic of the breathing rate, displaying the single heart rate as the heart rate or on determining of the single heart rate as the harmonic of the breathing rate, determining the heart rate based on a power signal, wherein the power signal is determined using a notch filter on the set of time series heart signals.

In an embodiment, determining the heart rate based on the power signal comprises of several steps that include comparing the power signal and the set of basic heart rate based on a pre-defined power threshold value and performing, based on the comparing, one of: displaying the single heart rate as the heart rate on determining the set of basic heart rate as less than the power signal by a pre-defined power threshold value or performing the frequency domain technique, the majority voting techniques and the harmonic detection technique for determination of the heart rate, on determining the set of basic heart rate as more than the power signal by the pre-defined power threshold value.

At step 1718 of the method (1700), includes displaying, by the one or more hardware processors, the determined heart rate and the determined breathing rate, wherein the determined heart rate and the determined breathing rate is indicative of the cardiopulmonary signals.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Experimental Results

The experiment has been conducted for in-body signal evaluation and testing for determination of cardiopulmonary signals. Five subjects are made to sit at different distances from the one or more UWB radar and breath normally. The input data received from one or more UWB radar has been processed using MatLab and for determining a ground truth of breathing rate and a ground truth for heart rate, video recording and PPG data was used simultaneously. The experimental data has been collated in the table below:

TABLE 1

Experimental data for determination of cardiopulmonary signals.

| Sl. No | Chest wall range bin | Breathing rate (breaths/minute) | Heart wall range bin | Heart rate calculated from heart wall range bin (beats/minute) |
|---|---|---|---|---|
| 1 | 162 | 17 | 183 | 70.82 |
| 2 | 207 | 21 | 228 | 65.76 |
| 3 | 175 | 22 | 196 | 64.07 |
| 4 | 173 | 15 | 194 | 75.03 |
| 5 | 208 | 14 | 229 | 74.19 |

Figure 18:
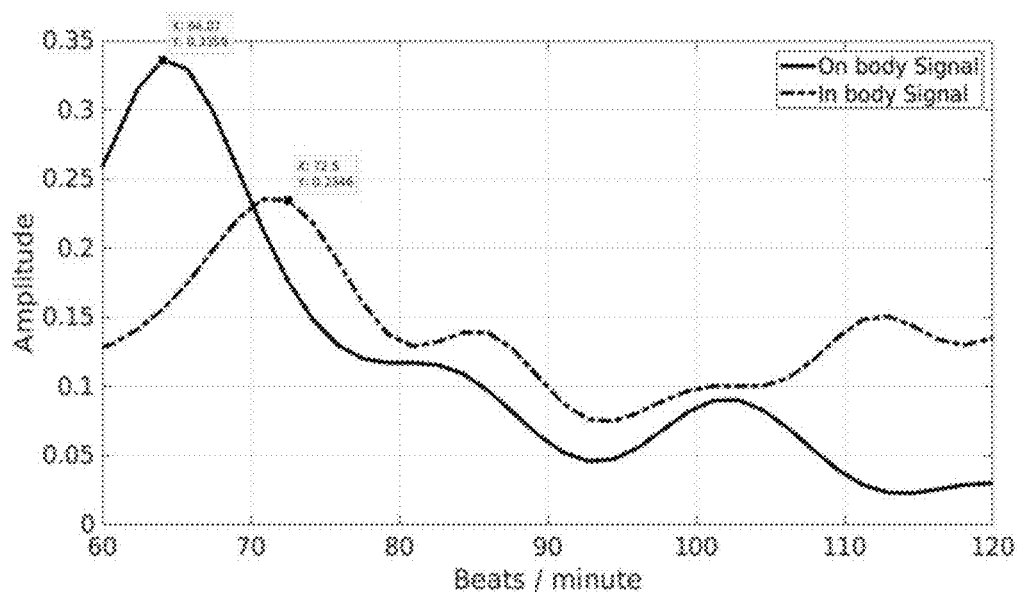
FIG. 18 illustrates a graph displaying a comparison of determination of heart rate using on body signal and in-body signal.

In an embodiment, the graph illustrated in FIG. 18 shows a use case comparison of determination of heart rate using on-body signals and in-body signals. The disclosed method and systems utilize in-body signals obtained by one or more UWB radars to determine cardiopulmonary signals that includes the heart rate and the breathing rate.

The embodiments of present disclosure herein address the problem of determination of cardiopulmonary signals for multi-persons. The disclosure herein generally relates to determination of cardiopulmonary signals for multi-persons using in-body signals obtained by one or more ultra-wide band (UWB) radar. The disclosed method determines of cardiopulmonary signals for multi-persons using in-body signals, wherein the UWB radar signals/waves reflected from inside a human body is utilized for efficient determination of cardiopulmonary signals. The disclosed method and system utilize the UWB radar signals to identify multi-persons along with several details about the persons that include a girth of the each identified person and the orientation of the identified person towards the one or more UWB radar. Further a chest wall distance, a breathing rate, a heart wall distance and a heart rate are determined for all the identified persons based on the identified girth and the identified orientation along with the UWB radar signals.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

We claim:

1. A processor-implemented method for determination of cardiopulmonary signals for multi-persons using in-body signals obtained by ultra-wide band (UWB) Radar, the method comprising:
    receiving by the one or more hardware processors, an input data set from one or more ultra-wideband (UWB) radars, wherein the input data is a plurality of UWB radar signals comprising 2-dimensional matrix indicative of a reflectance intensity at a range of the one of more UWB radars for a plurality of time instances;
    preprocessing by the one or more hardware processors, the input data set based on a filtering technique, a motion detection technique, and an envelope detection technique to obtain a pre-processed matrix, wherein the pre-processed matrix comprises of a plurality of range bins for the plurality of instances of range bin time;
    identifying by the one or more hardware processors, a plurality of persons in the vicinity of the one or more UWB radar and a girth for each person of the plurality of persons using the pre-processed matrix based on a peak identification technique, wherein the girth of the each person comprises of an entry point and an exit point, where the entry point and the exit point are indicative of a category of the person's body type;
    identifying by the one or more hardware processors, an orientation for each of the identified person of the plurality of persons using the pre-processed matrix based on a plurality of comparison techniques, wherein the orientation is indicative of the orientation of the identified person with respect to the one or more UWB radar, wherein the plurality of comparison techniques comprises an intensity comparison technique and a spectral flatness comparison technique;
    determining by the one or more hardware processors, a chest wall distance for each of the identified person of the plurality of persons using the pre-processed matrix based on the peak identification technique, wherein the chest wall distance is indicative of distance between the one or more UWB radar and each the identified person's chest wall;
    determining by the one or more hardware processors, a breathing rate for each of the identified person of the plurality of persons using the pre-processed matrix and the chest wall distance based on a plurality of auto-correlation technique, wherein the plurality of auto-correlation techniques are implemented on a set of time series of the range bins extracted from the pre-processed matrix using the chest wall distance;
    determining by the one or more hardware processors, a heart wall distance for each of the identified person of the plurality of persons and a heart wall range bin for each of the identified person of the plurality of persons based on a heart wall distance determination technique, wherein:
        the heart wall distance is indicative of distance between each of the identified person's chest wall and each of the identified person's heart wall and the heart wall distance is determined using a set of pre-defined dielectric constant of a plurality of biological tissues, a set of pre-defined wall values of the plurality of biological tissues, a pre-defined scaling factor for each of the biological tissue; and
        the heart wall range bin is indicative of a number of the range bin between each of the identified person's heart wall and the One or more UWB radar and the heart wall range bin is determined using the heart wall distance, the chest wall distance and a pre-determined range resolution of the one or more UWB radar;
    determining by the one or more hardware processors, a heart rate for each of the identified person of the plurality of persons using the pre-processed matrix, the heart wall distance and a pre-determined time resolution of the one or more UWB radar based on a heart rate determination technique, the heart rate determination technique comprises of a frequency domain technique and a harmonic removal technique; and
    displaying by the one or more hardware processors, the heart rate and the breathing rate, wherein the heart rate and the breathing rate is indicative of the cardiopulmonary signals.

2. The method of claim 1, wherein the pre-processing comprises:
    filtering the input data set based on the filtering technique to obtain a filtered input data set, wherein the filtering technique, comprise a bandpass filter of third order Infinite Impulse Response (IIR) filter with a pre-defined band pass in a pre-defined operating frequency range, wherein each of the 2-Dimensional matrix of the input data set is filtered along the range of the One or more UWB radar for each instant of time;

filtering the filtered input data set based on the motion filtering technique to obtain a motion filtered matrix, wherein the motion filtering technique comprises a second order difference filter;

determining an absolute matrix from the motion filtered matrix, wherein the absolute matrix is an absolute value of the motion filtered matrix; and filtering the absolute matrix based on the envelope detection technique to obtain a pre-processed matrix, wherein the envelope detection technique comprises of low pass butterworth filter.

3. The method of claim 1, wherein the identification of the number of persons and the girth for each person of the plurality of persons comprises:

computing a mean along one of the dimensions of the pre-processed matrix to obtain a mean matrix;

identifying a set of twin peak pairs in the mean matrix, wherein the twin peak pairs represent a person and the total number of peaks identified indicate a number of persons;

identifying a first peak and a second peak in each twin peak pair in the mean matrix, wherein the first peak indicates an entry point and the second peak indicates the exit point; and comparing the entry point and the exit point based on a pre-defined girth threshold range to identify the category of the person's body type, wherein the category of the person's body type comprises one of a thin body type, a medium body type and a fat body type, to determine the person's girth.

4. The method of claim 1, wherein the orientation includes a front facing position of the identified person with respect to the one or more UWB radar, a back facing position of the identified person with respect to the One or more UWB radar and a side facing position of the identified person with respect to the one or more UWB radar.

5. The method of claim 1, wherein the identification of the orientation based on the intensity comparison technique comprises:

computing a mean along a dimension of the pre-processed matrix to obtain a mean vector;

identifying a position mean in the mean vector that corresponds to the position of person to obtain an intensity value;

identifying the orientation of the identified person based on comparison of the intensity value with a pre-defined intensity threshold range wherein the orientation comprises a front facing position, a back facing position and a side facing position and the set of pre-defined orientation threshold ranges comprises an upper threshold (UT) and a lower threshold (LT); and performing the spectral flatness comparison technique if the intensity value lies between the UT and the LT.

6. The method of claim 5, wherein the spectral flatness comparison technique comprises:

identifying a girth mean vector in the mean vector that corresponds to the girth of person, wherein the girth mean comprises of a set of scanned values;

determining a peak flatness for each of the scanned values in the girth mean vector using the girth mean vector, a mean of power spectral density of the girth mean vector and a geometric mean of power spectral density of the girth mean vector; and comparing the peak flatness with the pre-defined intensity threshold range to identify the orientation of the identified person with respect to the One or more UWB radar.

7. The method of claim 1, wherein the determination of the chest wall distance using the pre-processed matrix based on the peak identification technique, comprises of identification of a plurality of peaks from the plurality of range bins of the pre-processed matrix, wherein a peak that is identified first among the plurality of peaks is indicative of the chest wall distance.

8. The method of claim 1, wherein the heart wall distance determination technique comprises of determination of the heart wall distance and the heart wall range bin, which can be expressed as shown below:

$$D = \alpha_1 W_1 \sqrt{\varepsilon_1} + \alpha_2 W_2 \sqrt{\varepsilon_2} + \ldots + \alpha_n W_n \sqrt{\varepsilon_n}$$

wherein
D is the heart wall distance
W is the biological tissue
$\alpha$ is a pre-defined scaling factor for each of the biological tissue
$\varepsilon$ dielectric constant of the biological tissue
n represents a "$n^{th}$" biological tissue $$B_{HR} = \left[ \frac{D}{Resol_{range}} \right] + B_{BR}$$

Wherein
$B_{HR}$ is the heart wall range bin
D is the heart wall distance
$Resol_{range}$ is the range resolution of One or more UWB radar
$B_{BR}$ is the chest wall distance.

9. The method of claim 1, wherein the heart rate determination technique comprises:

extracting a set of time series heart signals from the pre-processed matrix based on the heart wall range bin;

pre- processing the set of time series heart signals for removal of noise using noise removal techniques;

determining a set of basic heart rate from each of the set of pre-processed time series heart signals using a frequency domain technique;

identifying a single heart rate from the set of basic heart rate based on a majority voting techniques;

determining based on a harmonic detection technique, whether the single heart rate is a harmonic of the breathing rate; and performing, upon determining, one of:

on determining the single heart rate as not the harmonic of the breathing rate, displaying the single heart rate as the heart rate, and on determining of the single heart rate as the harmonic of the breathing rate, determining the heart rate based on a power signal, wherein the power signal is determined using a notch filter on the set of time series heart signals.

10. The method of claim 1, wherein determining the heart rate based on the power signal comprises:

comparing the power signal and the set of basic heart rate based on a pre-defined power threshold value; and performing based on the comparing, one of:

displaying the single heart rate as the heart rate on determining the set of basic heart rate as less than the power signal by a pre-defined power threshold value;

performing the frequency domain technique, the majority voting techniques and the harmonic detection technique for determination of the heart rate, on determining the set of basic heart rate as more than the power signal by the pre-defined power threshold value.

11. A system for determination of cardiopulmonary signals for multi-persons using in-body signals obtained by one or more UWB radar, comprising:
one or more memories;
one or more hardware processors,
an input/output interface; and
the one or more memories coupled to the one or more hardware processors, wherein the one or more hardware processors are configured to execute programmed instructions stored in the one or more memories to:
receive an input data set from one or more ultra-wideband (UWB) radars, wherein the input data is a UWB radar signal comprising 2-dimensional matrix indicative of a reflectance intensity at a range of the One or more UWB radar for a plurality of time instances;
preprocess the input data set based on a filtering technique, a motion detection technique, and an envelope detection technique to obtain a pre-processed matrix, wherein the pre-processed matrix comprises of a plurality of range bins for a plurality of instances of range bin time;
identify a number of persons in the vicinity of the One or more UWB radar and a girth for each of the person of the plurality of persons using the pre-processed matrix based on a peak identification technique, wherein the girth of the each person comprises of an entry point and an exit point, where the entry point and the exit point are indicative of a category of the person's body type;
identify, an orientation for each of the identified person of the plurality of persons using the pre-processed matrix based on a plurality of comparison techniques, wherein the orientation is indicative of the orientation of the identified person with respect to the one or more UWB radar, wherein the plurality of comparison techniques comprises an intensity comparison technique and a spectral flatness comparison technique;
determine, a chest wall distance for each of the identified person of the plurality of persons using the pre-processed matrix based on the peak identification technique, wherein the chest wall distance is indicative of distance between the one or more UWB radar and each the identified person's chest wall;
determine, a breathing rate for each of the identified person of the plurality of persons using the pre-processed matrix and the chest wall distance based on a plurality of auto-correlation technique, wherein the plurality of auto-correlation techniques are implemented on a set of time series of the range bins extracted from the pre-processed matrix using the chest wall distance;
determine, a heart wall distance for each of the identified person of the plurality of persons and a heart wall range bin for each of the identified person of the plurality of persons based on a heart wall distance determination technique, wherein:
the heart wall distance is indicative of distance between each of the identified person's chest wall and each of the identified person's heart wall and the heart wall distance is determined using a set of pre-defined dielectric constant of a plurality of biological tissues, a set of pre-defined wall values of the plurality of biological tissues, a pre-defined scaling factor for each of the biological tissue; and
the heart wall range bin is indicative of a number of the range bin between each of the identified person's heart wall and the One or more UWB radar and the heart wall range bin is determined using the heart wall distance, the chest wall distance and a pre-determined range resolution of the one or more UWB radar;
determine, a heart rate for each of the identified person of the plurality of persons using the pre-processed matrix, the heart wall distance and a pre-determined time resolution of the one or more UWB radar based on a heart rate determination technique, heart rate determination technique comprises of a frequency domain technique and a harmonic removal technique; and
display, the determined heart rate and the determined breathing rate, wherein the determined heart rate and the determined breathing rate is indicative of the cardiopulmonary signals.

12. The system of claim 11, wherein the heart wall distance determination technique are implemented by the one or more hardware processors that are further configured by the instructions to determine the heart wall distance and the heart wall range bin, which can be expressed as shown below:

$$D = \alpha_1 W_1 \sqrt{\varepsilon_1} + \alpha_2 W_2 \sqrt{\varepsilon_2} + \ldots + \alpha_n W_n \sqrt{\varepsilon_n}$$

wherein
D is the heart wall distance
α is a pre-defined scaling factor for each biological tissues
W is a biological tissue
ε dielectric constant of the biological tissue
n represents a "$n^{th}$" biological tissue $$B_{HR} = \left[ \frac{D}{Resol_{range}} \right] + B_{BR}$$

Wherein
$B_{HR}$ is the heart wall range bin
D is the heart wall distance
$Resol_{range}$ is the range resolution of One or more UWB radar
$B_{BR}$ is the chest wall distance.

13. The system of claim 11, wherein the heart rate determination technique are implemented by the one or more hardware processors that are further configured by the instructions for:
extracting a set of time series heart signals from the pre-processed matrix based on the heart wall range bin;
pre- processing the set of time series heart signals for removal of noise using noise removal techniques;
determination of a set of basic heart rate from each of the set of pre-processed time series heart signals using a frequency domain technique
identifying a single heart rate from the set of basic heart rate based on a majority voting techniques; and
determining, based on a harmonic detection technique, whether the single heart rate is a harmonic of the breathing rate;
performing, upon determining, one of:
on determining the single heart rate as not the harmonic of the breathing rate, displaying the single heart rate as the heart rate, and
on determining of the single heart rate as the harmonic of the breathing rate, determining the heart rate based on a power signal, wherein the power signal is determined using a notch filter on the set of time series heart signals.

14. The system of claim 11, wherein the step of determining the heart rate based on a power signal is implemented by the one or more hardware processors that are further configured by the instructions for:
comparing the power signal and the set of basic heart rate based on a pre-defined power threshold value; and
performing, based on the comparing, one of:
displaying the single heart rate as the heart rate on determining the set of basic heart rate as less than the power signal by a pre-defined power threshold value;
performing the frequency domain technique, the majority voting techniques and the harmonic detection technique for determination of the heart rate, on determining the set of basic heart rate as more than the power signal by the pre-defined power threshold value.

15. A non-transitory computer-readable medium having embodied thereon a computer readable program for determination of cardiopulmonary signals for multi-persons using in-body signals obtained by ultra-wide band (UWB) Radar wherein the computer readable program , when executed by one or more hardware processors, causes:
receiving an input data set from one or more ultra-wideband (UWB) radars, wherein the input data is a plurality of UWB radar signals comprising 2-dimensional matrix indicative of a reflectance intensity at a range of the one of more UWB radars for a plurality of time instances;
preprocessing the input data set based on a filtering technique, a motion detection technique, and an envelope detection technique to obtain a pre-processed matrix, wherein the pre-processed matrix comprises of a plurality of range bins for the plurality of instances of range bin time;
identifying a plurality of persons in the vicinity of the one or more UWB radar and a girth for each person of the plurality of persons using the pre-processed matrix based on a peak identification technique, wherein the girth of the each person comprises of an entry point and an exit point, where the entry point and the exit point are indicative of a category of the person's body type;
identifying an orientation for each of the identified person of the plurality of persons using the pre-processed matrix based on a plurality of comparison techniques, wherein the orientation is indicative of the orientation of the identified person with respect to the one or more UWB radar, wherein the plurality of comparison techniques comprises an intensity comparison technique and a spectral flatness comparison technique;
determining a chest wall distance for each of the identified person of the plurality of persons using the pre-processed matrix based on the peak identification technique, wherein the chest wall distance is indicative of distance between the one or more UWB radar and each the identified person's chest wall;
determining a breathing rate for each of the identified person of the plurality of persons using the pre-processed matrix and the chest wall distance based on a plurality of auto-correlation technique, wherein the plurality of auto-correlation techniques are implemented on a set of time series of the range bins extracted from the pre-processed matrix using the chest wall distance;
determining a heart wall distance for each of the identified person of the plurality of persons and a heart wall range bin for each of the identified person of the plurality of persons based on a heart wall distance determination technique, wherein:
the heart wall distance is indicative of distance between each of the identified person's chest wall and each of the identified person's heart wall and the heart wall distance is determined using a set of pre-defined dielectric constant of a plurality of biological tissues, a set of pre-defined wall values of the plurality of biological tissues, a pre-defined scaling factor for each of the biological tissue; and
the heart wall range bin is indicative of a number of the range bin between each of the identified person's heart wall and the One or more UWB radar and the heart wall range bin is determined using the heart wall distance, the chest wall distance and a pre-determined range resolution of the one or more UWB radar;
determining, by the one or more hardware processors, a heart rate for each of the identified person of the plurality of persons using the pre-processed matrix, the heart wall distance and a pre-determined time resolution of the one or more UWB radar based on a heart rate determination technique, the heart rate determination technique comprises of a frequency domain technique and a harmonic removal technique; and
displaying, by the one or more hardware processors, the heart rate and the breathing rate, wherein the heart rate and the breathing rate is indicative of the cardiopulmonary signals.

* * * * *